United States Patent
Ditter et al.

(10) Patent No.: US 9,220,433 B2
(45) Date of Patent: Dec. 29, 2015

(54) CATHETER WITH VARIABLE ARCUATE DISTAL SECTION

(75) Inventors: Tom Allen Ditter, Chino Hills, CA (US); Diana Gallardo, Perris, CA (US); Shahram Moaddeb, Irvine, CA (US); Michael Olen Zirkle, Yorba Linda, CA (US)

(73) Assignee: Biosense Webster (Israel), LTD., Yokneam (IL)

( * ) Notice: Subject to any disclaimer, the term of this patent is extended or adjusted under 35 U.S.C. 154(b) by 926 days.

(21) Appl. No.: 13/174,742

(22) Filed: Jun. 30, 2011

(65) Prior Publication Data
US 2013/0006238 A1 Jan. 3, 2013

(51) Int. Cl.
*A61B 18/14* (2006.01)
*A61B 5/042* (2006.01)
(Continued)

(52) U.S. Cl.
CPC .............. *A61B 5/0422* (2013.01); *A61B 5/0538* (2013.01); *A61B 5/6857* (2013.01);
(Continued)

(58) Field of Classification Search
USPC ................................. 606/41, 49; 604/20, 530
See application file for complete search history.

(56) References Cited

U.S. PATENT DOCUMENTS

| | | | |
|---|---|---|---|
| 3,971,364 A | | 7/1976 | Fletcher et al. |
| 4,488,561 A | * | 12/1984 | Doring .......................... 607/125 |

(Continued)

FOREIGN PATENT DOCUMENTS

| | | |
|---|---|---|
| DE | 197 50 441 A1 | 6/1999 |
| EP | 0 856 292 A1 | 8/1998 |

(Continued)

OTHER PUBLICATIONS

European Patent Office Extended Search Report for EP 12178339.3, dated Dec. 13, 2012, 8 pgs.

(Continued)

*Primary Examiner* — Jospeh Stoklosa
*Assistant Examiner* — Jocelyn D Ram
(74) *Attorney, Agent, or Firm* — Christie, Parker & Hale, LLP

(57) ABSTRACT

A catheter includes an elongated body, a distal assembly with a shape-memory member defining a generally circular form, and a control handle adapted to actuate a deflection puller wire for deflecting a portion of the elongated body, and a contraction wire for contracting the generally circular form. The generally circular form which carries at least one ring electrode has an off-edge configuration relative to the elongated body such that a longitudinal axis of the elongated body does not intersect the circumference of the circular form and the generally circular form spirals about the longitudinal axis of the elongated body. Moreover, the circular form can have an on-axis configuration such that the longitudinal axis of the elongated body is axially aligned with a central longitudinal axis of the circular form, or an off-axis configuration such that these axes are axially offset from each other. In a more detailed embodiment, the catheter has a distal assembly with a helical form or a crescent form carrying a plurality of irrigated ablation ring electrodes and a plurality of smaller ring electrodes adapted for impedance recording or PV potential recording. A support member with shape memory extends through the distal assembly to provide the helical or crescent form. The support member has a varying stiffness along its length, for example, a decreasing stiffness toward a distal end of the support member. The support member can also be hollow so that it can receive a mandrel whose stiffness is greater than that of the support member.

14 Claims, 15 Drawing Sheets

(51) Int. Cl.
*A61B 5/00* (2006.01)
*A61B 5/053* (2006.01)
*A61B 17/00* (2006.01)
*A61B 18/00* (2006.01)
*A61B 5/06* (2006.01)
*A61B 19/00* (2006.01)

(52) U.S. Cl.
CPC ............. *A61B18/1492* (2013.01); *A61B 5/062* (2013.01); *A61B 2017/00867* (2013.01); *A61B 2018/00029* (2013.01); *A61B 2018/00357* (2013.01); *A61B 2018/00375* (2013.01); *A61B 2018/00577* (2013.01); *A61B 2018/00821* (2013.01); *A61B 2018/00875* (2013.01); *A61B 2018/1407* (2013.01); *A61B 2018/1432* (2013.01); *A61B 2018/1435* (2013.01); *A61B 2018/1467* (2013.01); *A61B 2019/465* (2013.01); *A61B 2019/5251* (2013.01); *A61B 2019/5263* (2013.01); *A61B 2217/007* (2013.01)

(56) References Cited

U.S. PATENT DOCUMENTS

| | | | |
|---|---|---|---|
| 4,764,114 A | 8/1988 | Jeffcoat et al. | |
| 4,856,993 A | 8/1989 | Maness et al. | |
| 4,917,102 A * | 4/1990 | Miller et al. | 600/585 |
| 4,917,104 A | 4/1990 | Rebell | |
| 5,263,493 A | 11/1993 | Avitall | |
| 5,334,193 A | 8/1994 | Nardella | |
| 5,368,564 A | 11/1994 | Savage | |
| 5,391,199 A | 2/1995 | Ben-Haim | |
| 5,403,311 A | 4/1995 | Abele et al. | |
| 5,487,757 A | 1/1996 | Truckai et al. | |
| 5,499,542 A | 3/1996 | Morlan | |
| 5,558,091 A | 9/1996 | Acker et al. | |
| 5,563,354 A | 10/1996 | Kropp | |
| 5,643,197 A | 7/1997 | Brucker et al. | |
| 5,662,124 A | 9/1997 | Wilk | |
| 5,673,695 A | 10/1997 | McGee et al. | |
| 5,680,860 A * | 10/1997 | Imran | 600/374 |
| 5,685,878 A | 11/1997 | Falwell et al. | |
| 5,697,927 A | 12/1997 | Imran et al. | |
| 5,718,701 A | 2/1998 | Shai et al. | |
| 5,730,127 A | 3/1998 | Avitall | |
| 5,769,843 A | 6/1998 | Abela et al. | |
| 5,820,591 A | 10/1998 | Thompson et al. | |
| 5,826,576 A | 10/1998 | West | |
| 5,836,894 A | 11/1998 | Sarvazyan | |
| 5,860,920 A | 1/1999 | McGee et al. | |
| 5,860,974 A | 1/1999 | Abele | |
| 5,865,815 A | 2/1999 | Tihon | |
| 5,871,523 A | 2/1999 | Fleischman et al. | |
| 5,876,398 A | 3/1999 | Mulier et al. | |
| 5,902,248 A | 5/1999 | Millar et al. | |
| 5,913,854 A * | 6/1999 | Maguire et al. | 606/41 |
| 5,916,147 A | 6/1999 | Boury | |
| 5,938,694 A * | 8/1999 | Jaraczewski et al. | 607/122 |
| 5,944,022 A | 8/1999 | Nardella et al. | |
| 5,964,757 A | 10/1999 | Ponzi | |
| 5,974,320 A | 10/1999 | Ward et al. | |
| 5,983,126 A | 11/1999 | Wittkampf | |
| 6,002,955 A * | 12/1999 | Willems et al. | 600/374 |
| 6,048,329 A | 4/2000 | Thompson et al. | |
| 6,063,022 A | 5/2000 | Ben-Haim | |
| 6,064,902 A | 5/2000 | Haissaguerre et al. | |
| 6,123,699 A | 9/2000 | Webster, Jr. | |
| 6,171,277 B1 | 1/2001 | Ponzi | |
| 6,177,792 B1 | 1/2001 | Govari et al. | |
| 6,183,463 B1 | 2/2001 | Webster, Jr. | |
| 6,198,974 B1 | 3/2001 | Webster, Jr. | |
| 6,201,387 B1 | 3/2001 | Govari | |
| 6,203,493 B1 | 3/2001 | Ben-Haim | |
| 6,216,027 B1 | 4/2001 | Willis et al. | |
| 6,226,542 B1 | 5/2001 | Reisfeld | |
| 6,239,724 B1 | 5/2001 | Doron et al. | |
| 6,241,724 B1 | 6/2001 | Fleischman et al. | |
| 6,267,781 B1 | 7/2001 | Tu | |
| 6,272,371 B1 | 8/2001 | Shlomo | |
| 6,272,672 B1 | 8/2001 | Conway | |
| 6,301,496 B1 | 10/2001 | Reisfeld | |
| 6,332,089 B1 | 12/2001 | Acker et al. | |
| 6,335,617 B1 | 1/2002 | Osadchy et al. | |
| 6,371,955 B1 | 4/2002 | Fuimaono et al. | |
| 6,436,059 B1 | 8/2002 | Zanelli | |
| 6,456,864 B1 | 9/2002 | Swanson et al. | |
| 6,468,260 B1 | 10/2002 | Bumbalough et al. | |
| 6,484,118 B1 | 11/2002 | Govari | |
| 6,500,167 B1 | 12/2002 | Webster, Jr. | |
| 6,522,930 B1 | 2/2003 | Schaer et al. | |
| 6,522,933 B2 | 2/2003 | Nguyen | |
| 6,551,302 B1 | 4/2003 | Rosinko et al. | |
| 6,574,492 B1 | 6/2003 | Ben-Haim et al. | |
| 6,584,856 B1 | 7/2003 | Biter et al. | |
| 6,592,581 B2 | 7/2003 | Bowe | |
| 6,602,242 B1 | 8/2003 | Fung et al. | |
| 6,612,992 B1 | 9/2003 | Hossack et al. | |
| 6,618,612 B1 | 9/2003 | Acker et al. | |
| 6,638,275 B1 | 10/2003 | McGaffigan et al. | |
| 6,669,692 B1 * | 12/2003 | Nelson et al. | 606/41 |
| 6,690,963 B2 | 2/2004 | Ben-Haim et al. | |
| 6,695,808 B2 | 2/2004 | Tom | |
| 6,706,039 B2 | 3/2004 | Mulier et al. | |
| 6,711,429 B1 | 3/2004 | Gilboa et al. | |
| 6,712,815 B2 | 3/2004 | Sampson et al. | |
| 6,723,094 B1 | 4/2004 | Desinger | |
| 6,727,371 B2 | 4/2004 | Müller et al. | |
| 6,814,733 B2 | 11/2004 | Schwartz et al. | |
| 6,835,173 B2 | 12/2004 | Couvillon, Jr. | |
| 6,892,091 B1 | 5/2005 | Ben-Haim et al. | |
| 6,908,464 B2 | 6/2005 | Jenkins et al. | |
| 6,911,019 B2 | 6/2005 | Mulier et al. | |
| 6,915,149 B2 | 7/2005 | Ben-Haim | |
| 6,945,956 B2 | 9/2005 | Waldhauser et al. | |
| 6,964,205 B2 | 11/2005 | Papakostas et al. | |
| 6,973,339 B2 | 12/2005 | Govari | |
| 6,984,232 B2 * | 1/2006 | Vanney et al. | 606/41 |
| 6,987,995 B2 * | 1/2006 | Drysen | 600/374 |
| 6,997,924 B2 | 2/2006 | Schwartz et al. | |
| 7,008,401 B2 | 3/2006 | Thompson et al. | |
| 7,008,418 B2 | 3/2006 | Hall et al. | |
| 7,077,823 B2 | 7/2006 | McDaniel | |
| 7,104,989 B2 | 9/2006 | Skarda | |
| 7,156,816 B2 | 1/2007 | Schwartz et al. | |
| 7,235,070 B2 | 6/2007 | Vanney | |
| 7,276,061 B2 * | 10/2007 | Schaer et al. | 607/41 |
| 7,285,116 B2 | 10/2007 | de la Rama et al. | |
| 7,285,119 B2 | 10/2007 | Stewart et al. | |
| 7,306,593 B2 | 12/2007 | Keidar et al. | |
| 7,311,704 B2 | 12/2007 | Paul et al. | |
| 7,397,364 B2 | 7/2008 | Govari | |
| 7,419,489 B2 | 9/2008 | Vanney et al. | |
| 7,481,774 B2 | 1/2009 | Brockway et al. | |
| 7,496,394 B2 | 2/2009 | Ahmed et al. | |
| 7,517,349 B2 | 4/2009 | Truckai et al. | |
| 7,536,218 B2 | 5/2009 | Govari et al. | |
| 7,591,816 B2 | 9/2009 | Wang et al. | |
| 7,604,605 B2 | 10/2009 | Zvuloni | |
| 7,681,432 B2 | 3/2010 | Hay et al. | |
| 7,686,767 B2 | 3/2010 | Maschke | |
| 7,850,685 B2 | 12/2010 | Kunis et al. | |
| 8,066,702 B2 * | 11/2011 | Rittman et al. | 606/41 |
| 8,083,691 B2 | 12/2011 | Goldenberg et al. | |
| 8,359,082 B2 | 1/2013 | Selkee | |
| 8,628,526 B2 | 1/2014 | Laufer et al. | |
| 8,747,351 B2 | 6/2014 | Schultz | |
| 8,798,706 B2 * | 8/2014 | Kim et al. | 600/374 |
| 2001/0007070 A1 * | 7/2001 | Stewart et al. | 606/41 |
| 2001/0047129 A1 | 11/2001 | Hall et al. | |
| 2001/0047133 A1 | 11/2001 | Gilboa et al. | |
| 2002/0002329 A1 | 1/2002 | Avitall | |
| 2002/0022839 A1 | 2/2002 | Stewart et al. | |

(56) References Cited

U.S. PATENT DOCUMENTS

| | | | |
|---|---|---|---|
| 2002/0065455 A1 | 5/2002 | Ben-Haim et al. | |
| 2002/0068866 A1 | 6/2002 | Zikorus et al. | |
| 2002/0165461 A1 | 11/2002 | Hayzelden et al. | |
| 2002/0169444 A1* | 11/2002 | Mest et al. | 606/41 |
| 2002/0193781 A1 | 12/2002 | Loeb | |
| 2003/0050637 A1* | 3/2003 | Maguire et al. | 606/41 |
| 2003/0105453 A1 | 6/2003 | Stewart et al. | |
| 2003/0120195 A1 | 6/2003 | Milo et al. | |
| 2003/0125726 A1* | 7/2003 | Maguire et al. | 606/41 |
| 2003/0130615 A1 | 7/2003 | Tom | |
| 2003/0158494 A1 | 8/2003 | Dahl et al. | |
| 2003/0216722 A1 | 11/2003 | Swanson | |
| 2004/0049255 A1 | 3/2004 | Jain et al. | |
| 2004/0064024 A1 | 4/2004 | Sommer | |
| 2004/0068178 A1 | 4/2004 | Govari | |
| 2004/0082948 A1 | 4/2004 | Stewart et al. | |
| 2004/0097806 A1 | 5/2004 | Hunter et al. | |
| 2004/0102769 A1 | 5/2004 | Schwartz et al. | |
| 2004/0143175 A1 | 7/2004 | Coleman et al. | |
| 2004/0147920 A1 | 7/2004 | Keidar | |
| 2004/0152974 A1 | 8/2004 | Solomon | |
| 2004/0158141 A1 | 8/2004 | Scheib | |
| 2004/0244464 A1 | 12/2004 | Hajdukiewicz et al. | |
| 2004/0254458 A1 | 12/2004 | Govari | |
| 2005/0004565 A1 | 1/2005 | Vanney | |
| 2005/0010095 A1 | 1/2005 | Stewart et al. | |
| 2005/0033135 A1 | 2/2005 | Govari | |
| 2005/0070894 A1 | 3/2005 | McClurken | |
| 2005/0080429 A1 | 4/2005 | Freyman et al. | |
| 2005/0165388 A1 | 7/2005 | Bhola | |
| 2005/0187544 A1 | 8/2005 | Swanson et al. | |
| 2005/0277875 A1 | 12/2005 | Selkee | |
| 2006/0009690 A1 | 1/2006 | Fuimaono et al. | |
| 2006/0009735 A1 | 1/2006 | Viswanathan et al. | |
| 2006/0015096 A1 | 1/2006 | Hauck et al. | |
| 2006/0020264 A1 | 1/2006 | Crowley et al. | |
| 2006/0106295 A1* | 5/2006 | Jais et al. | 600/374 |
| 2006/0173480 A1 | 8/2006 | Zhang | |
| 2006/0200049 A1 | 9/2006 | Leo et al. | |
| 2006/0235381 A1 | 10/2006 | Whayne et al. | |
| 2006/0247618 A1 | 11/2006 | Kaplan et al. | |
| 2006/0253116 A1 | 11/2006 | Avitall et al. | |
| 2007/0021742 A1 | 1/2007 | Viswanathan | |
| 2007/0060832 A1 | 3/2007 | Levin | |
| 2007/0060847 A1 | 3/2007 | Leo et al. | |
| 2007/0100332 A1 | 5/2007 | Paul et al. | |
| 2007/0106114 A1 | 5/2007 | Sugimoto et al. | |
| 2007/0142749 A1 | 6/2007 | Khatib et al. | |
| 2007/0151391 A1 | 7/2007 | Larkin et al. | |
| 2007/0156114 A1 | 7/2007 | Worley et al. | |
| 2007/0161882 A1 | 7/2007 | Pappone | |
| 2007/0179492 A1 | 8/2007 | Pappone | |
| 2007/0185397 A1 | 8/2007 | Govari et al. | |
| 2007/0191829 A1 | 8/2007 | McGee et al. | |
| 2007/0197939 A1 | 8/2007 | Wallace et al. | |
| 2007/0282211 A1 | 12/2007 | Ofek et al. | |
| 2008/0009750 A1 | 1/2008 | Aeby et al. | |
| 2008/0015568 A1 | 1/2008 | Paul et al. | |
| 2008/0051704 A1 | 2/2008 | Patel et al. | |
| 2008/0065111 A1 | 3/2008 | Blumenkranz et al. | |
| 2008/0071267 A1 | 3/2008 | Wang et al. | |
| 2008/0077049 A1 | 3/2008 | Hirshman | |
| 2008/0097394 A1 | 4/2008 | Lampropoulos et al. | |
| 2008/0161774 A1* | 7/2008 | Hastings et al. | 604/524 |
| 2008/0161795 A1 | 7/2008 | Wang et al. | |
| 2008/0161803 A1* | 7/2008 | Oral et al. | 606/41 |
| 2008/0183075 A1 | 7/2008 | Govari et al. | |
| 2008/0249522 A1 | 10/2008 | Pappone et al. | |
| 2008/0255540 A1 | 10/2008 | Selkee | |
| 2008/0275428 A1 | 11/2008 | Tegg et al. | |
| 2008/0275442 A1 | 11/2008 | Paul et al. | |
| 2008/0275465 A1 | 11/2008 | Paul et al. | |
| 2008/0281319 A1 | 11/2008 | Paul et al. | |
| 2008/0287777 A1 | 11/2008 | Li et al. | |
| 2008/0288038 A1 | 11/2008 | Paul et al. | |
| 2008/0294144 A1 | 11/2008 | Leo et al. | |
| 2008/0294158 A1 | 11/2008 | Pappone et al. | |
| 2009/0010021 A1 | 1/2009 | Smith et al. | |
| 2009/0062787 A1 | 3/2009 | Schaer et al. | |
| 2009/0093806 A1 | 4/2009 | Govari et al. | |
| 2009/0138007 A1 | 5/2009 | Govari et al. | |
| 2009/0158511 A1 | 6/2009 | Maze et al. | |
| 2009/0254083 A1 | 10/2009 | Wallace et al. | |
| 2009/0287118 A1 | 11/2009 | Malek | |
| 2009/0306650 A1 | 12/2009 | Govari et al. | |
| 2010/0030209 A1 | 2/2010 | Govari et al. | |
| 2010/0063478 A1 | 3/2010 | Selkee | |
| 2010/0137845 A1 | 6/2010 | Ramstein et al. | |
| 2010/0145423 A1 | 6/2010 | Seifert | |
| 2010/0152574 A1 | 6/2010 | Erdman et al. | |
| 2010/0168548 A1* | 7/2010 | Govari et al. | 600/374 |
| 2010/0168620 A1 | 7/2010 | Klimovitch et al. | |
| 2010/0168918 A1 | 7/2010 | Zhao et al. | |
| 2010/0222851 A1 | 9/2010 | Deem et al. | |
| 2010/0222859 A1 | 9/2010 | Govari et al. | |
| 2011/0034989 A1 | 2/2011 | Al-Marashi et al. | |
| 2011/0054287 A1 | 3/2011 | Schultz | |
| 2011/0054446 A1* | 3/2011 | Schultz | 604/528 |
| 2011/0118582 A1 | 5/2011 | De la Rama et al. | |
| 2011/0130648 A1 | 6/2011 | Beeckler et al. | |
| 2011/0144639 A1 | 6/2011 | Govari | |
| 2011/0160719 A1* | 6/2011 | Govari et al. | 606/41 |
| 2011/0184406 A1 | 7/2011 | Selkee | |
| 2011/0264011 A1* | 10/2011 | Wu et al. | 601/2 |
| 2012/0053403 A1 | 3/2012 | Ducharme et al. | |
| 2012/0116200 A1* | 5/2012 | Roy et al. | 600/374 |
| 2012/0116382 A1 | 5/2012 | Ku et al. | |
| 2012/0143088 A1 | 6/2012 | Schultz | |
| 2012/0172703 A1 | 7/2012 | Esguerra et al. | |
| 2012/0245577 A1* | 9/2012 | Mihalik et al. | 606/33 |
| 2012/0323174 A1* | 12/2012 | Shih | 604/95.04 |
| 2013/0165922 A1* | 6/2013 | Falwell et al. | 606/41 |
| 2013/0304062 A1* | 11/2013 | Chan et al. | 606/41 |
| 2014/0249525 A1* | 9/2014 | Scheib | 606/41 |
| 2014/0296845 A1* | 10/2014 | Miller et al. | 606/41 |

FOREIGN PATENT DOCUMENTS

| | | |
|---|---|---|
| EP | 0 928 601 A1 | 7/1999 |
| EP | 1 042 990 A1 | 10/2000 |
| EP | 1 181 896 A1 | 2/2002 |
| EP | 1 502 555 A1 | 2/2005 |
| EP | 1 586 281 A1 | 10/2005 |
| EP | 1 690 564 A1 | 8/2006 |
| EP | 1 743 575 A2 | 1/2007 |
| EP | 1 820 464 A1 | 8/2007 |
| EP | 1 897 581 A2 | 3/2008 |
| EP | 2 000 789 A2 | 12/2008 |
| EP | 2 047 797 A2 | 4/2009 |
| EP | 2 127 604 A1 | 12/2009 |
| EP | 2 130 508 A2 | 12/2009 |
| EP | 2 171 240 | 4/2010 |
| EP | 2 229 904 A1 | 9/2010 |
| EP | 2 263 588 A2 | 12/2010 |
| EP | 2 289 403 A1 | 3/2011 |
| EP | 2 289 408 A1 | 3/2011 |
| EP | 2 338 411 A1 | 6/2011 |
| EP | 2 338 412 A1 | 6/2011 |
| EP | 2-380 518 A2 | 10/2011 |
| EP | 2 540 245 A1 | 1/2013 |
| JP | 2005-345215 A | 12/2005 |
| JP | 2006-064465 A | 3/2006 |
| WO | WO 95/10326 A1 | 4/1995 |
| WO | WO 96/05768 | 2/1996 |
| WO | WO 97/29678 A2 | 8/1997 |
| WO | WO 97/29709 A1 | 8/1997 |
| WO | WO 97/29710 A1 | 8/1997 |
| WO | WO 98/29032 A1 | 7/1998 |
| WO | WO 99/56812 | 11/1999 |
| WO | WO 03/020139 A2 | 3/2003 |
| WO | WO 2006/003216 A1 | 1/2006 |
| WO | WO 2006/029563 A1 | 3/2006 |
| WO | WO 2006/086152 A2 | 8/2006 |
| WO | WO 2006/092563 A1 | 9/2006 |

(56) References Cited

FOREIGN PATENT DOCUMENTS

| WO | WO 2007/025230 A2 | 3/2007 |
|---|---|---|
| WO | WO 2007/050960 A2 | 5/2007 |
| WO | WO 2007/067938 A2 | 6/2007 |
| WO | WO 2007/082216 A1 | 7/2007 |
| WO | WO 2007/098494 A1 | 8/2007 |
| WO | WO 2007/111182 A1 | 10/2007 |
| WO | WO 2009/078280 A1 | 6/2009 |
| WO | WO 2009/085470 A1 | 7/2009 |
| WO | WO 2009/147399 A1 | 12/2009 |
| WO | WO 2010/008975 A2 | 1/2010 |

OTHER PUBLICATIONS

European Patent Office Search Report for EP 12178339.3, dated Oct. 31, 2012, 5 pgs.

Biter, W.J. et al., "Magnetic Wire Strain Sensor," 33rd International SAMPE Technical Conference, Nov. 5-8, 2001, vol. 33, Cover pg. and pp. 12-23, Seattle, WA.

Biter, W.J. et al., "Magnetic Wire for Monitoring Strain in Composites," Sensors, Jun. 2001, www.sensormag.com, pp. 110-114.

Okumura, Y. et al., "A Systematic Analysis of In Vivo Contact Forces on Virtual Catheter Tip/Tissue Surface Contact During Cardiac Mapping and Intervention," *Journal of Cardiovascular Electrophysiology*, vol. 19, No. 6, pp. 632-640, Jun. 2008.

European Search Report for Application No. EP 12174272.0, dated Sep. 25, 2012, 6 pages.

European Search Report completed Aug. 14, 2013 for European Patent Application No. 13167733, 3 pages.

European Examination Report dated Nov. 25, 2014 for European Patent Application No. 13167733.8, 8 pages.

Chinese Office action dated Mar. 5, 2014 in Chinese Application No. 201010624677.4, English language translation only, 14 pages.

Russian Office action dated Nov. 14, 2013 in Russian Application No. 2009149447/14(073080) with English translation, 12 pages.

Russian Office action dated Dec. 5, 2013 in Russian Application No. 2012127341/15(042535), English language translation only, 3 pages.

\* cited by examiner

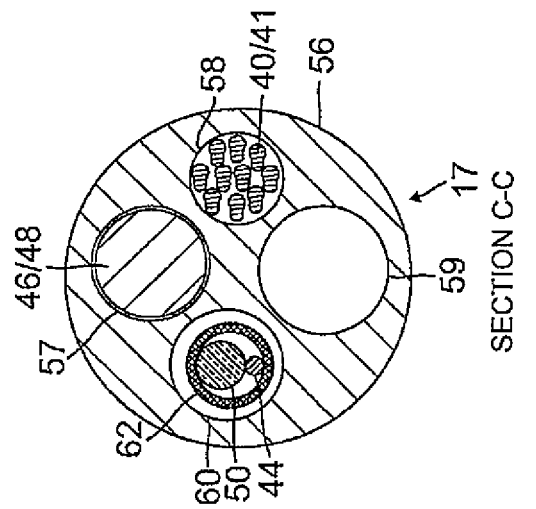
FIG. 11
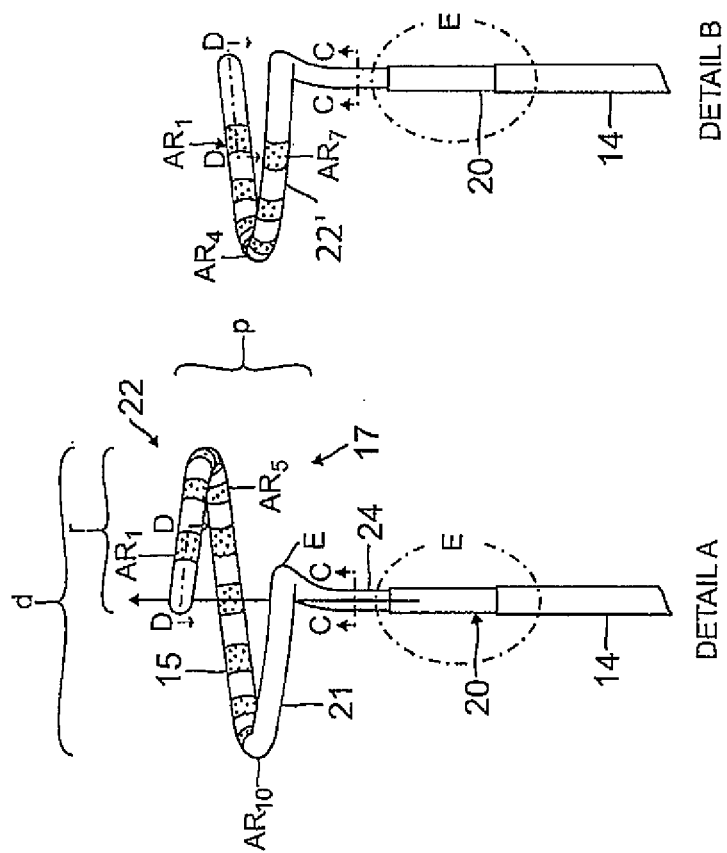
FIG. 19
FIG. 7

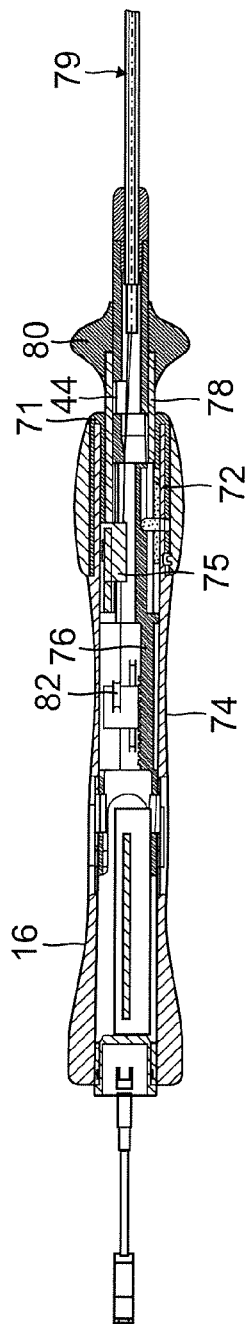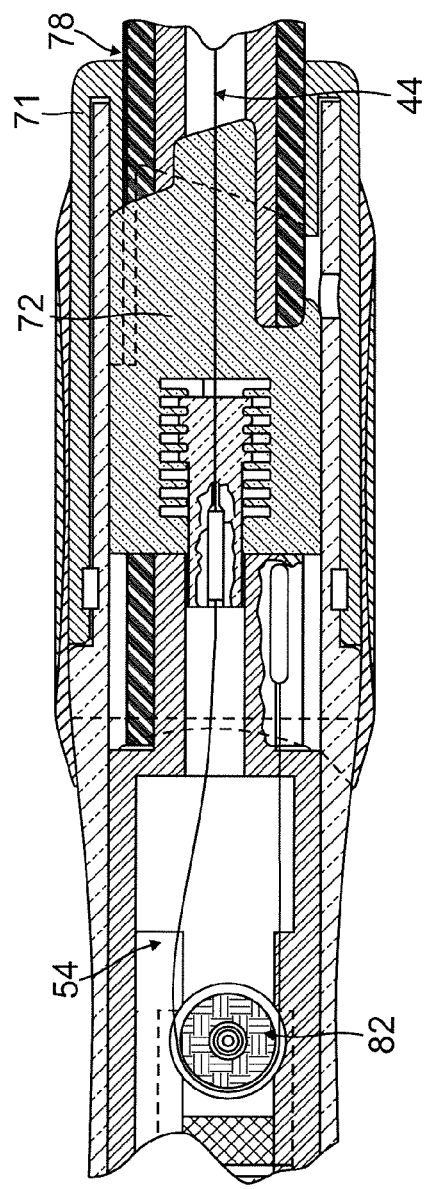
FIG. 16
FIG. 17

CATHETER WITH VARIABLE ARCUATE DISTAL SECTION

FIELD OF INVENTION

This invention relates generally to methods and devices for invasive medical treatment, and specifically to catheters, in particular, catheters having distal sections adapted for mapping and ablating selected anatomy.

BACKGROUND

Ablation of myocardial tissue is well known as a treatment for cardiac arrhythmias. In radio-frequency (RF) ablation, for example a catheter is inserted into the heart and brought into contact with tissue at a target location. RF energy is then applied through an electrode on the catheter in order to create a lesion for the purpose of breaking arrhythmogenic current paths in the tissue.

Recently, circumferential ablation of the ostia of the pulmonary vein has gained acceptance as a treatment for atrial arrhythmias, and particularly for atrial fibrillation. For example, U.S. Pat. No. 6,064,902, whose disclosure is incorporated herein by reference, describes a catheter for ablating tissue on the inner wall of a blood vessel, such as a pulmonary vein. The tip portion of the catheter is deflectable from a first, generally straight, configuration, in which the proximal and distal sections are substantially co-linear, to a second, J-shaped, configuration in which the proximal and distal sections are generally parallel with a separation therebetween substantially corresponding to the inside diameter of the blood vessel. The distal end portion of the catheter is rotated about the longitudinal axis of the catheter to cause a circumferential displacement of proximal and distal ablation electrodes on the catheter along the inner wall of the pulmonary vein. In this way, the electrode catheter may be used to ablate a number of circumferentially-spaced sites on the inner wall of the pulmonary vein by ablating one or two sites at each circumferential position.

U.S. Patent Application Publication 2005/0033135, whose disclosure is incorporated herein by reference, describes a lasso for pulmonary vein mapping and ablation. A catheter for circumferentially mapping a pulmonary vein (PV) includes a curved section shaped to generally conform to the shape of the interior surface of the PV. The curved section is connected to catheter by a generally straight axial base section that is in an "on edge" configuration where the base axial section connects to the curved section on the circumference of the curved section. The curved section comprises one or more sensing electrodes, and its proximal end is joined at a fixed or generally known angle to a base section of the catheter. Position sensors are fixed to the curved section of the catheter and to the distal end of the base section. The catheter is inserted into the heart, and the curved section is positioned in contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV. The sensing electrodes may additionally perform ablation of selected sites, or the catheter may further comprise ablation elements.

U.S. Pat. No. 7,008,401, whose disclosure is incorporated herein by reference, describes compound steering assemblies, usable in both diagnostic and therapeutic applications, for steering the distal section of a catheter in multiple planes or complex curves. These assemblies are said to enable a physician to swiftly and accurately position and maintain ablation and/or mapping electrodes in intimate contact with an interior body surface. U.S. Pat. No. 5,820,591, whose disclosure is incorporated herein by reference, similarly describes compound steering assemblies of this sort.

U.S. application Ser. No., 12/649,417 now U.S. Patent Application Publication No. 2011/0160719, filed on Dec. 30, 2009, whose disclosure is incorporated herein by reference, describes a medical device, including an insertion shaft, having a longitudinal axis and having a distal end adapted for insertion into a body of a patient. A resilient end section is fixed to the distal end of the insertion shaft and is formed so as to define, when unconstrained, an arc oriented obliquely relative to the axis and having a center of curvature on the axis. One or more electrodes are disposed at respective locations along the end section.

However, because human anatomy varies between individuals, the shape and size of an ostium vary, and the end section whether having an arcuate shape or a generally circular shape may not always fit the particular target ostium. Moreover, because the right atrium is a confined volume, the approach into a PV ostium is often times indirect in that the base section does not always assume a perpendicular angle to the target site. Because of these factors, contact between the electrodes and the ostium is often less than complete.

Accordingly, a desire exists for a lasso-type catheter that can provide an end section whose curved (or circular, used interchangeably herein) portion can be varied to fit differently-sized ostia. Moreover, by providing an end section with a curved portion that is supported "off-edge" by the catheter, the curved portion is better adapted to distribute the load for more complete tissue contact when an axial force is applied to the catheter during mapping or ablation. Furthermore, the curved portion can be supported either "on axis" or off-axis" by the catheter, where an on-axis configuration may be better suited for a straight-on approach toward an ostium and an off-axis configuration may be better suited for an angled approach toward an ostium. There is also a further desire for such catheter to provide accurate tissue contact verification and/or accurate visualization of PV potentials during ablation with the use impedance and/or PV potential recording electrodes.

SUMMARY OF THE INVENTION

The present invention is directed to a catheter whose distal assembly has a curved (or circular) configuration that can be varied by means of a contraction wire actuated by a control handle and/or the use of a mandrel that is inserted into the distal assembly. For improved surface contact between the electrodes and the target tissue, e.g., a PV ostium, the distal assembly includes a radially transverse section that supports the electrode-bearing curved portion of the distal assembly in an "off-edge" manner which allows a better, more controlled distribution of load on the electrode-bearing curved portion when an axial force is applied to the catheter during mapping and/or ablation. The electrode-bearing curved portion of the distal assembly may be centered on the catheter where it is supported in an "on axis" manner such that a center of the curved portion is on or axially aligned with a longitudinal axis of the catheter. Alternatively, the electrode-bearing curved portion is supported in an "off-axis" manner where the center of the curved portion is axially offset from the longitudinal axis of the catheter.

The configuration of the electrode-bearing portion of the distal assembly is generally curved or circular, including a helical form or a crescent shape, for mapping and/or ablating tubular regions, such as a PV ostium. The helical form is tapered, either expanding in radius or decreasing in radius along its spiral. A support member with shape memory provides the desired configuration in the distal assembly and its flexibility can vary along its length. For example, the helical form may be stiffer in the proximal portion for withstanding load and more flexible in the distal portion for easier contraction. Such variable stiffness can be accomplished by varying the thickness of the support member, such as having a thicker proximal portion and a thinner distal portion.

To minimize the risk of charring, ablation ring electrodes carried on the distal assembly are irrigated. The ablation ring electrode has an enlarged mid-section so as to provide an annular gap or reservoir around the tubing carrying the ring electrode so that flow distribution to outside the electrode through apertures in the side wall of the ablation ring electrode is improved. Apertures are also provided in opposing end portions of the ring electrodes so that irrigation flows in the radial direction, as well as in the axial direction.

Whereas a contraction wire can be actuated via the control handle to contract the distal assembly, a mandrel can be inserted through the distal assembly, or in particular, through the support member, to vary or alter the form of the electrode-bearing curved portion of the distal assembly. To facilitate this adjustment or variation, the support member can be hollow so as to receive the mandrel therethrough. To increase flexibility of the support member so that it can yield to the predetermined form of the mandrel while maintaining sufficient rigidity so that it can return its own predetermined form in the absence or withdrawal of the mandrel, the support member may be formed from a bundle of wires coiled in a spiral, or it may be a tubular member with a spiral cut along its length. The spiral cut may be smooth, or it may have an interlocking pattern such that the support member provides the desired flexibility without elongation in the axial direction.

The electrode-bearing portion of the distal assembly may include smaller and/or more closely spaced-together ring electrodes for impedance and/or PV potential recording. Accordingly, a single catheter can perform simultaneous ablation, mapping (electrogram recording) and assessment of tissue contact.

In one embodiment, the catheter includes an elongated body, and a distal assembly with a shape-memory member defining a generally circular form. The catheter further includes a control handle adapted to actuate a deflection puller wire for deflecting a portion of the elongated body, and a contraction wire for contracting the generally circular form. The generally circular form which carries at least one ring electrode has an off-edge configuration relative to the elongated body such that a longitudinal axis of the elongated body does not intersect the circumference of the circular form and the generally circular form spirals about the longitudinal axis of the elongated body. Moreover, the circular form can have an on-axis configuration such that the longitudinal axis of the elongated body is axially aligned with a central longitudinal axis of the circular form, or an off-axis configuration such that these axes are axially offset from each other.

In a more detailed embodiment, the catheter has a distal assembly with a helical form or a crescent form carrying a plurality of irrigated ablation ring electrodes and a plurality of smaller ring electrodes adapted for impedance recording or PV potential recording. A control handle has a first control member that draws a contraction wire for contracting the helical or crescent form, and a second control member that draws a deflection wire for deflecting an intermediate section proximal of the distal assembly. A support member with shape memory extends through the distal assembly to provide the helical or crescent form. The support member has a varying stiffness along its length, for example, a decreasing stiffness toward a distal end of the support member.

In another more detailed embodiment, the support member is hollow so that it can receive a mandrel whose stiffness is greater than that of the support member so that the support member can yield to and generally assume the predetermined form of the mandrel. The support member may be of a hollow strand tube construction, or it may be a tubular construction with a spiral cut with either a smooth pattern or an interlocking pattern.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 4A is a side view of an embodiment of a distal assembly approaching an ostium straight on.

FIG. 7 is a detailed perspective view of the distal end portion of the catheter of FIG. 1, as delineated by line A-A.

FIG. 11 is an end cross-sectional view of a section of the distal end portion of FIG. 7, taken along line C-C.

FIG. 16 is a side cross-sectional view of the control handle of FIG. 1, taken along line L-L.

FIG. 17 is a partial detailed view of the control handle of FIG. 16.

FIG. 19 is a detailed perspective view of the distal end portion of the catheter of FIG. 18, as delineated by line B-B.

DETAILED DESCRIPTION OF THE INVENTION

Lasso catheters, as described above, may be used for mapping and ablating tissue along an arc or curve surrounding an anatomical structure, such as the ostium of a pulmonary vein. The lasso is generally made thin and flexible, for purposes of maneuverability, with large ring electrodes to minimize electrical resistance. U.S. patent application Ser. No. 12/345,720, now U.S. Patent Application Publication No. 2010/0168548, filed Dec. 30, 2008, which is assigned to the assignee of the present patent application and whose disclosure is incorporated herein by reference, describes an alternative design in which the lasso is thicker and stiffer. Even so, operators can find lasso catheters to be difficult to maneuver within the heart and position in such a way that the entire circumference of the lasso is in contact with the tissue, as is desirable for effective pulmonary vein isolation.

Embodiments of the present invention that are described hereinbelow provide probes, such as catheters, with improved lasso-type structures to facilitate maneuvering and positioning in the heart. Such catheters can be used to produce curved, circular, looped or otherwise closed ablation paths, as well as sensing electrical activity along a curve, circle, loop or closed pattern for electrical potential and anatomical mapping.

Figure 1:
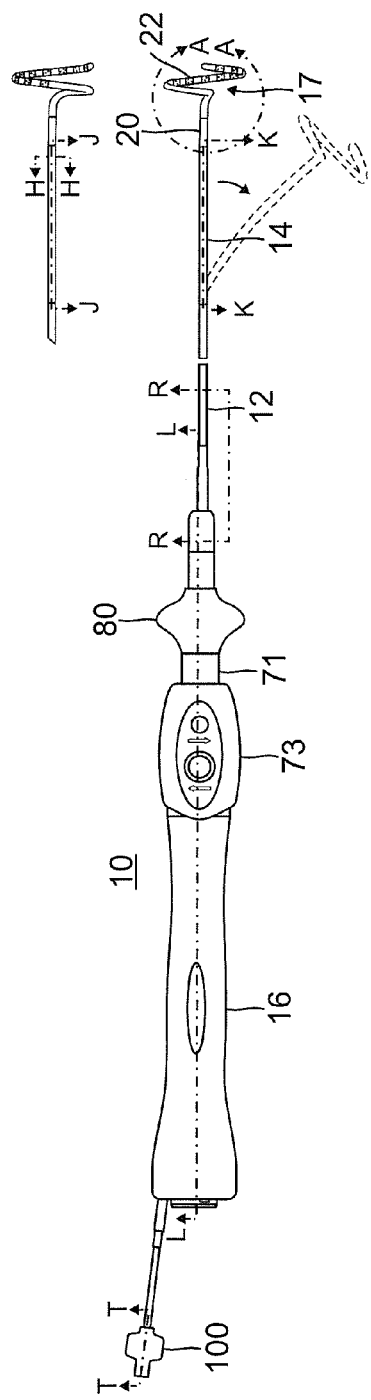
FIG. 1 is a top plan view of an embodiment of a catheter in accordance with the present invention.
Figure 2:
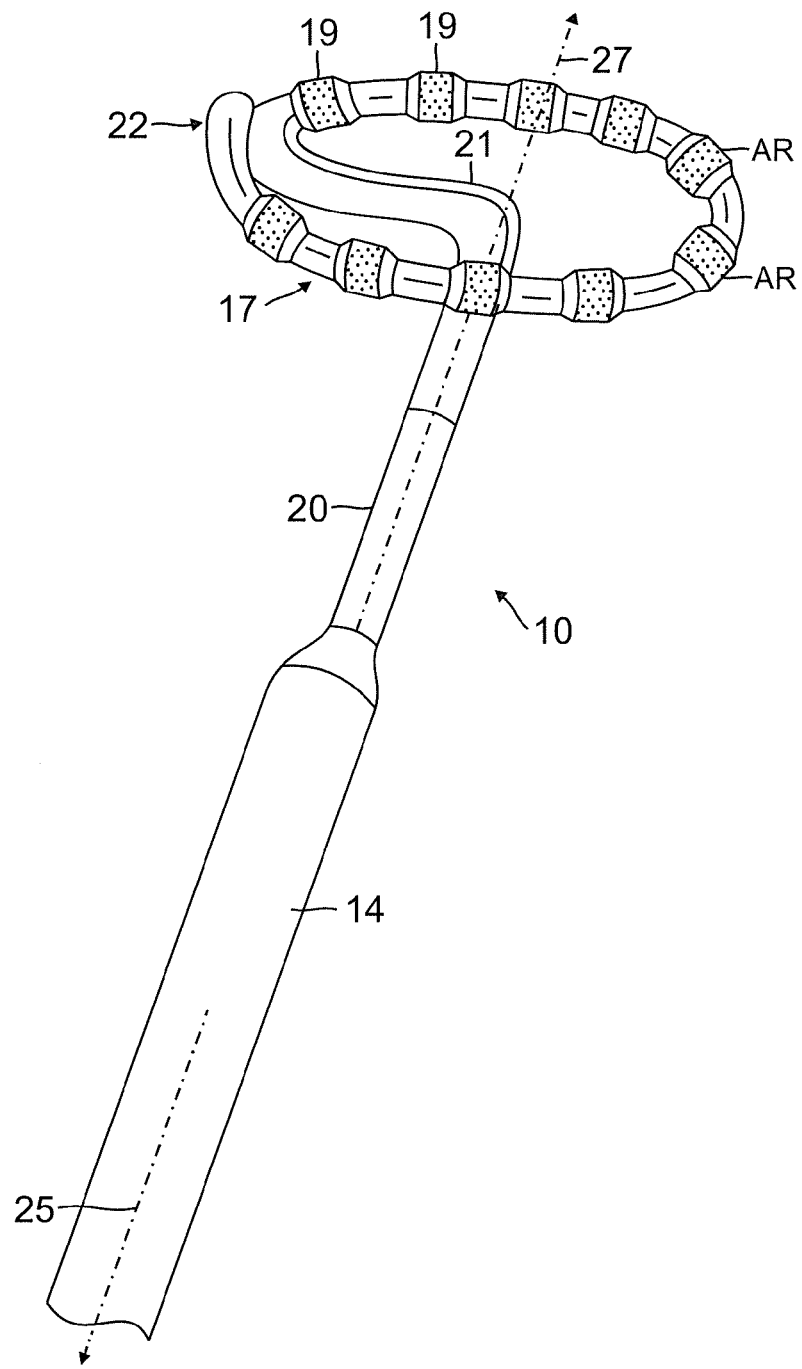
FIG. 2 is a perspective view of an embodiment of a distal end portion of a catheter of the present invention, including a distal assembly.

Referring to FIGS. 1 and 2, a catheter 10 according to the disclosed embodiments comprises an elongated body that may include an insertion shaft or catheter body 12 having a longitudinal axis, and an intermediate section 14 distal of the catheter body that can be uni- or bi-directionally deflected off axis from the catheter body longitudinal axis. A resilient three-dimensional distal assembly 17, with ring electrodes 19 disposed along a nonlinear or curved distal portion, extends from a generally straight transitional section 20 distal of the elongated body or the intermediate section 14. In accordance with a feature of the present invention, the curved distal portion defines, when unconstrained, a generally helical form 22. The helical form is oriented obliquely relative to a longitudinal axis 25 of the intermediate section 14. The term "obliquely", in the context of the present invention means that the plane in space that best fits the helical form is angled relative to the longitudinal axis 25 of the intermediate section 14. The angle between the plane and the axis ranges between about 45 to 105 degrees, preferably between about 75 to 105 degrees, and more preferably about 90 degrees. Moreover, the helical form spirals or subtends in a predetermined manner. In one embodiment, the helical form subtends about 360 degrees. In another embodiment, the helical form subtends greater than 360 degrees, e.g., about 380 degrees.

Figure 3:
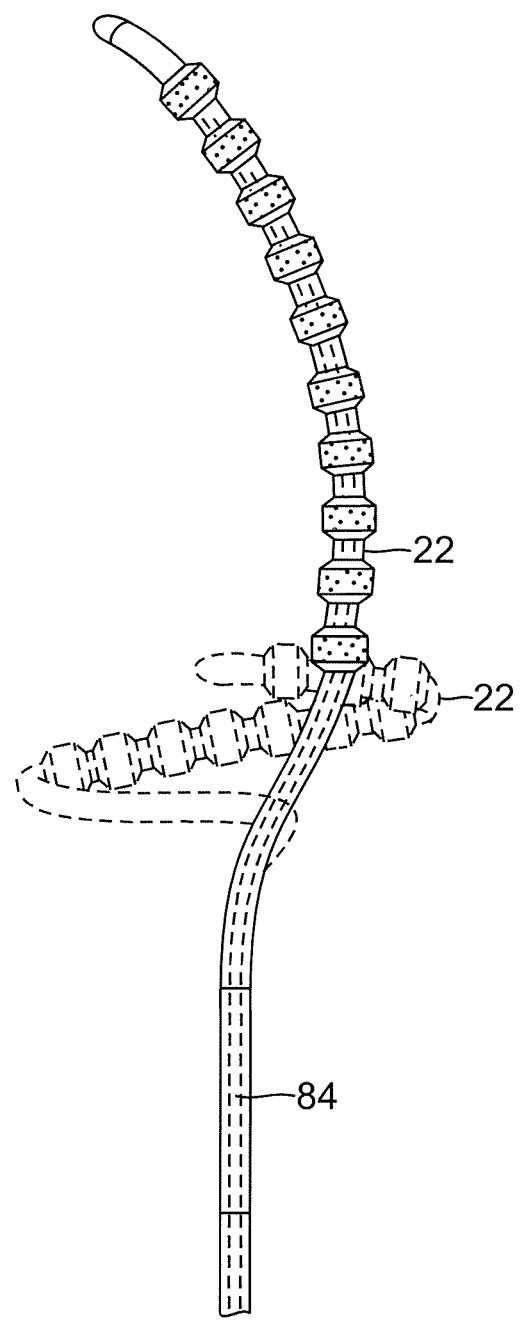
FIG. 3 is a perspective view of an embodiment of a distal assembly.

Advantageously, the catheter 10 is designed to allow the helical form 22 to be contracted, thus decreasing its radius and/or pitch, by an operator manipulating a control handle 16 at the proximal end of the catheter body 12, as explained below in further detail. Furthermore, as illustrated in FIG. 3, the present catheter allows the overall configuration of the helical form 22 to be varied and adjusted, including significant expansion, whereby the helical form can be generally straightened, by means of a mandrel member 84 that is inserted alongside with or through a shape-memory member 50 that provides the helical form 22 of the distal assembly 17, as also explained below in further detail.

Figure 4A:
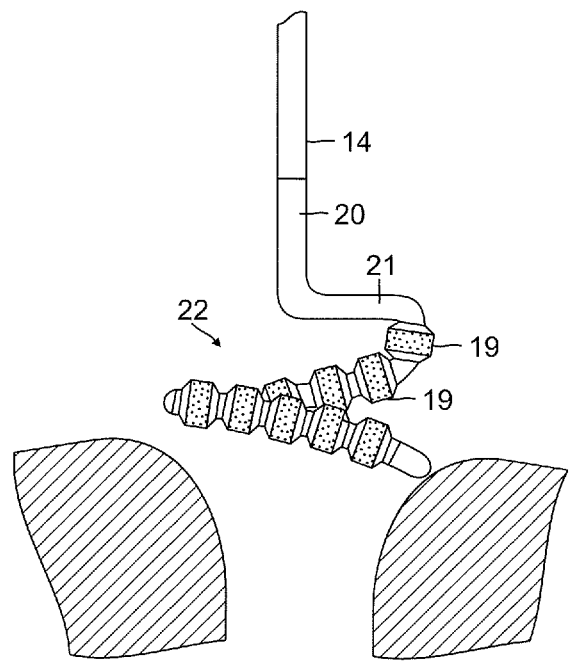
Figure 4B:
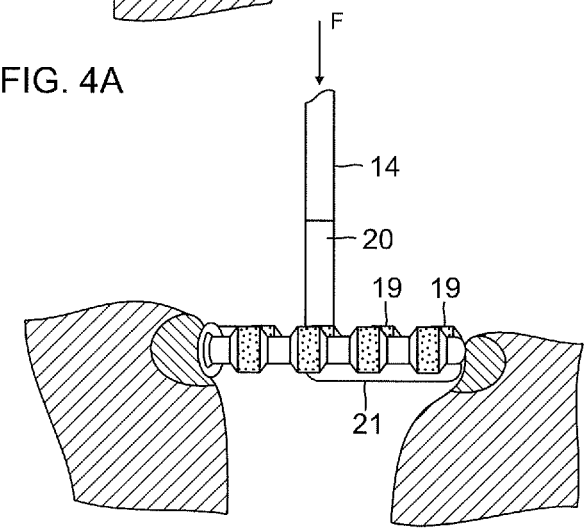
FIG. 4B is a side view of the distal assembly of FIG. 4A in contact with the ostium.

The catheter enters a patient's body through a guiding sheath that has been inserted in a body cavity, such as a heart chamber. Due to the flexible construction of the distal assembly 17, the helical form 22 readily straightens for insertion into the guiding sheath. The distal assembly is advanced axially in the guiding sheath until it moves past the distal end of the guiding sheath toward a tissue in the body, such as the inner heart wall. (The term "axial" refers to the direction parallel to the longitudinal axis of the catheter). When exposed and unconstrained, the distal assembly 17 reassumes the helical form 22 which is maneuvered to engage the tissue surface frontally with some or all of the electrodes 19 on the helical form contacting the tissue surface simultaneously, as shown in FIGS. 4A and 4B.

As discussed in detail further below, if the ostium is smaller in diameter than the helical form in its natural relaxed state, the operator can contract the helical form by means of a contraction wire manipulated via the control handle. If the ostium if larger in diameter than the helical form, the operator can expand or even significantly straighten the helical form by advancing a mandrel into the helical form that is straighter and stiffer than the shape-memory member of the helical form. In that regard, it is further understood that by providing a mandrel that is stiffer than the shape-memory member of the helical form, the form can generally assume the configuration or shape of the mandrel over the configuration of the shape-memory member.

According to an embodiment of the present invention, the catheter 10 has a three-dimensional mapping and/or ablation assembly 17 at its distal end. As shown in FIG. 1, the catheter comprises an elongated catheter body 12 having proximal and distal ends, a deflectable intermediate section 14, a control handle 16 at the proximal end of the catheter body, and a distal lasso-type assembly 17 mounted at the distal end of the deflectable intermediate section.

Figure 5A:
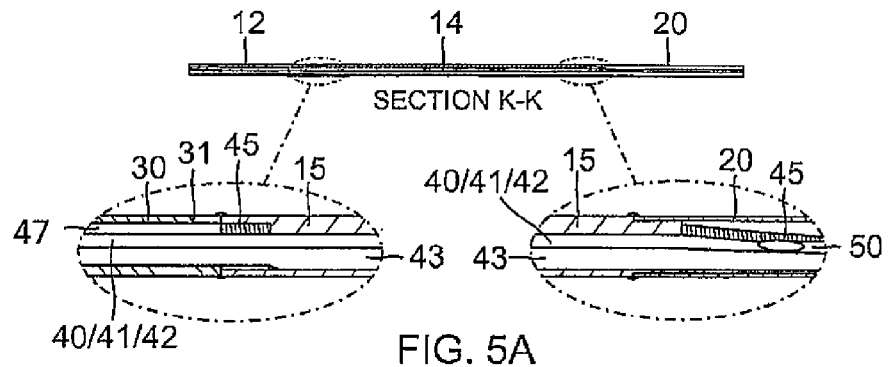
FIG. 5A is a side cross-sectional view of the catheter of FIG. 1, taken along line J-J.
Figure 5B:
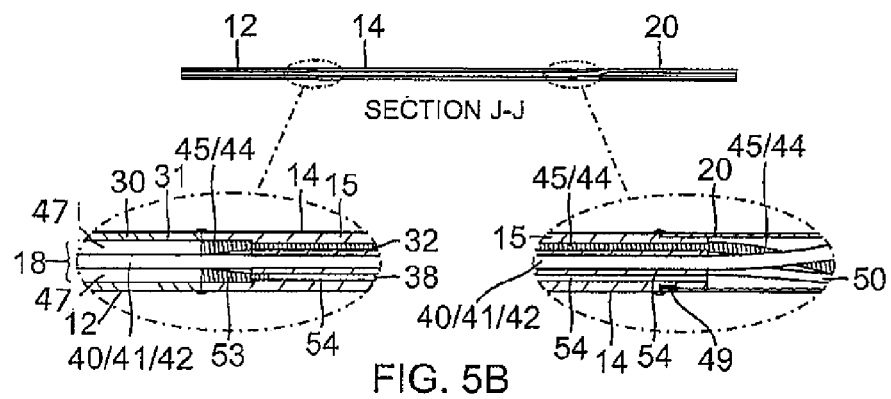
FIG. 5B is a side cross-sectional view of the catheter of FIG. 1, taken along line K-K.

In the depicted embodiment of FIGS. 5A and 5B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal assembly 17 will rotate in a corresponding manner.

The outer diameter of the catheter body 12 is not critical, but is preferably no more than about 8 french, more preferably 7 french. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

Figure 6:
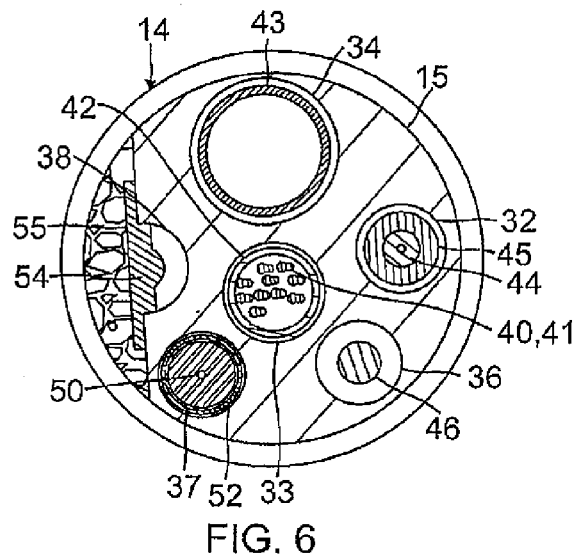
FIG. 6 is an end cross-sectional view of the catheter of FIG. 1, taken along line H-H.

The deflectable intermediate section 14 comprises a short section of tubing 15 having multiple lumens, each occupied by the various components extending through the intermediate section. In the illustrated embodiment of FIG. 6, there are six lumens. Lead wire/thermocouple pairs 40,41 for each ring electrode pass through a first lumen 33. A nonconductive protective sheath 42 may be provided. Irrigation tubing 43 for delivering irrigation fluid to the distal assembly 17 passes through a second lumen 34. A contraction wire 44 passes through a third lumen 32. A cable 46 for a position sensor assembly 48, including a plurality of single axis sensors (SAS) positioned on the distal assembly 17, passes through a fourth lumen 36. For the distal assembly 17, a shape-memory support member 50 surrounded by a nonconductive tubing 52, e.g., a polyimide tubing, extends proximally from the distal assembly 17 for a relatively short distance into a fifth lumen 37. A puller wire 54 for deflecting the intermediate section 14 passes through a sixth lumen 38.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the position of the third lumen 32 for the distal assembly contraction wire 44 is preferably more aligned with an inner circumference of the helical form 22 of the distal assembly 17 so that proximal movement of the wire can readily contract the helical form. Moreover, the sixth lumen 38 for the deflection wire 54 is off-axis so that distal movement of the deflection wire accomplishes deflection toward the side on which lumen is off axis. Preferably, the third and sixth lumens 32 and 38 are diametrically opposed to each other.

The useful length of the catheter, i.e., that portion that can be inserted into the body excluding the distal assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIG. 5. The proximal end of the intermediate section 14 comprises an inner circumferential notch that receives the outer surface of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Figure 8:
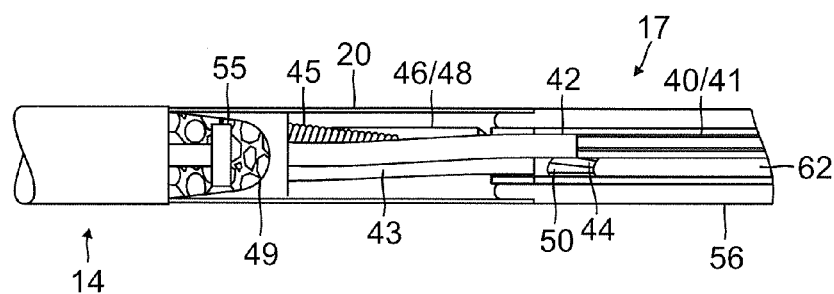
FIG. 8 is a side cross-sectional view of a section of the distal end portion of FIG. 7, as delineated by line E-E.

Distal the intermediate section 14 is the distal assembly 17. Extending between the intermediate section 14 and the distal assembly 17 is a transitional section 20, as shown in FIGS. 5 and 8, having a tubing of suitable material, e.g., PEEK, with a central lumen that allows the various components extending therethrough to reorient before entering the distal assembly 17.

Figure 9C:
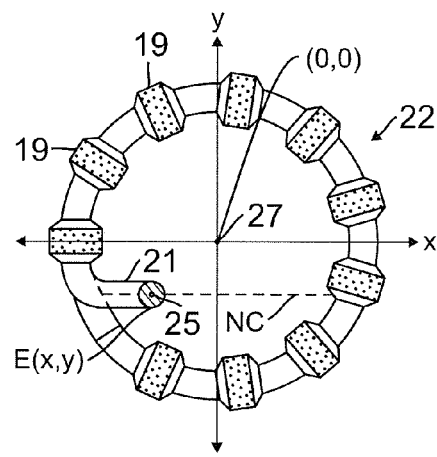
FIG. 9C is an end view of a third embodiment of a distal assembly, with an off-edge, off axis configuration.

As shown in FIG. 7, at a base of the helical form 22, the distal assembly 17 includes a generally straight proximal section 24 and a generally straight transverse section 21. The distal end of the proximal portion 24 and the proximal end of the transverse portion form an "elbow" E at their junction such that the transverse portion 21 is generally transverse to the longitudinal axis 25 of the catheter 10 or at least the intermediate section 14. In accordance with a feature of the present invention, the helical form 22 is mounted on the catheter in an "off-edge" configuration, where longitudinal axis 25 of the intermediate section 14 does not intersect the circumference of the helical form 22 but rather extends through the interior of the helical form as shown in FIGS. 9A-9C.

Figure 9A:
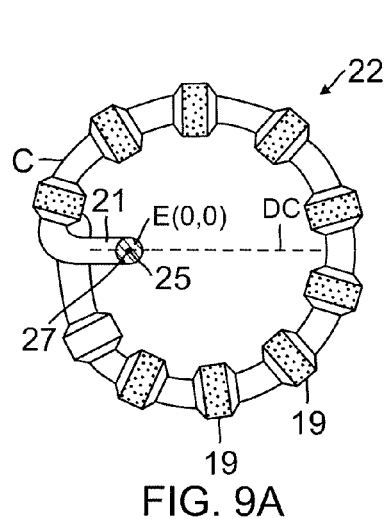
FIG. 9A is an end view of a first embodiment of a distal assembly, with an off-edge, on axis configuration.
Figure 9B:
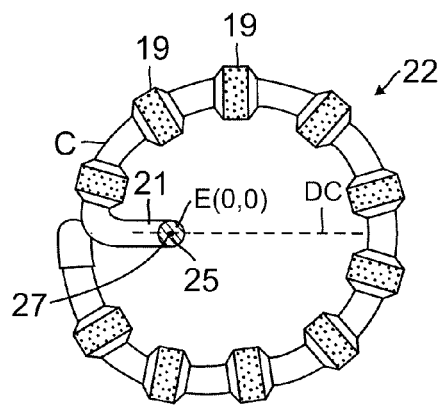
FIG. 9B is an end view of a second embodiment of a distal assembly, with an off-edge, on axis configuration.

In the embodiments of FIGS. 9A and 9B, center longitudinal axis 27 of the helical form 22 is generally aligned with the longitudinal axis 25 of the intermediate section, that is, the helical form 22 is axially centered ("on axis") on the longitudinal axis 25 of the intermediate section 14. In the embodiment of FIG. 9C, the respective longitudinal axes 25, 27 are parallel and offset or off alignment relative to each other such that the helical form 22 is "off axis" relative to the longitudinal axis 25. Where the interior of the helical form is defined by a centered X/Y Cartesian coordinate system, the elbow E generally assumes the central (0,0) position in an on-axis configuration, and an $(x \neq 0, y \neq 0)$ position in an off-axis configuration. The transverse section 21 can have any length between about zero and the diameter of the helical form and can lie on any diametrical chord DC (FIGS. 9A and 9B) or nondiametrical chord NC (FIG. 9C).

With reference to FIG. 7, the helical form 22 can be defined by a radius r (or diameter d) and a pitch P (number of turns per unit length along its longitudinal axis). The diameter suitable for mapping or ablating a PV ostium can range between about 20 mm and 35 mm. The pitch can range between about 0.5" and 0.3".

In accordance with a feature of the present invention, the helical form 22 is tapered along its length. In one embodiment, the helical form spirals outwardly with an increasing radius from its proximal end to its distal end (FIG. 9B). In another embodiment, the helical form spirals inwardly with a decreasing radius from its proximal end to its distal end (FIG. 9A). In yet another embodiment, the helical form has a generally constant radius along its length (FIG. 9C).

Figures 10A, 10B:
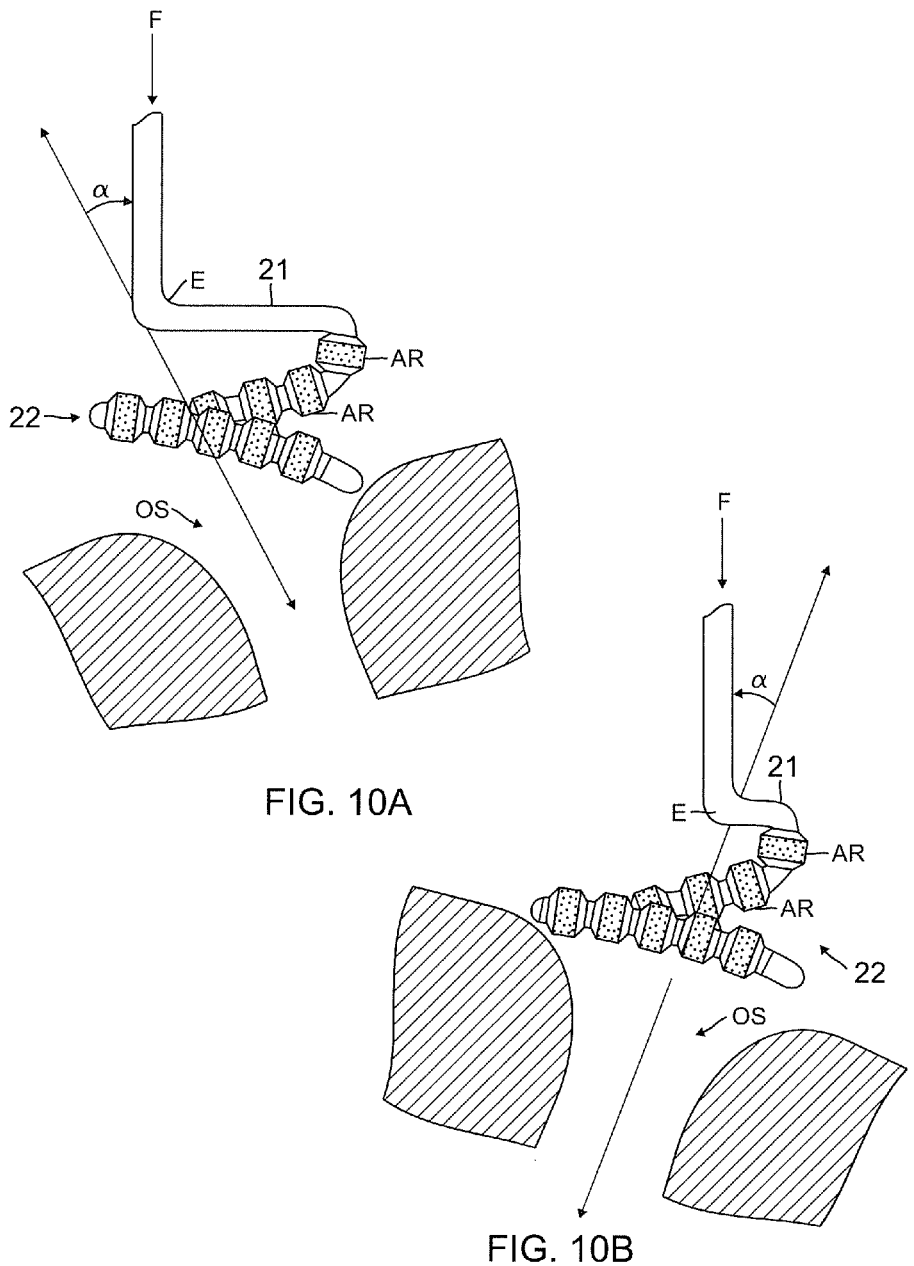
FIG. 10A is a side view of an embodiment of an off-axis distal assembly approaching an ostium from one angle.
FIG. 10B is a side view of another embodiment of an off-axis distal assembly approaching an ostium from an opposite angle.

Depending on the arrangement of the transverse section 21, including variations on the (x,y) position of the elbow E, different contact properties may be achieved with the distal assembly 17. For example, a distal assembly with an on-axis helical form 22 may be better suited for a head-on approach to an ostium OS (FIG. 4B) where angle α between the longitudinal axes of the ostium and the catheter ranges between 0 and 15 degrees. An off-axis helical form 22 may be better suited for an off-angle approach to an ostium OS (FIGS. 10A and 10B) where angle α is greater than about 15 degrees. As shown in FIGS. 10A and 10B, an off-axis helical form 22 may provide better tissue/electrode contact when a head-on approach to a target ostium is not possible. When an axial force F is applied to the catheter, the distal assembly may be able to better distribute the force for greater surface contact between the electrodes and the ostium. In FIG. 10A, the length of the transverse section 21 is greater than the radius of the helical form. In FIG. 10B the length of the transverse section 21 is lesser than the radius of the helical form.

In the illustrated embodiment of FIG. 7, the helical form 22 extends distally from the transverse section 21 and generally spirals about a longitudinal axis of the proximal section 24. The helical form 22 has an outer diameter d preferably ranging to about 33 mm to about 35 mm. The helical form 22 can curve in a clockwise direction or a counterclockwise direction. The proximal section 24 of the distal assembly 17 has an exposed length of about 5 mm. The transverse section 21 has an exposed length of about 28 mm. The helical form has an exposed length of about 76 mm.

As shown in FIG. 11, the distal assembly 17 is formed of multi-lumened tubing 56 which can be preformed with a desirable shape, including the helical form, as understood by one of ordinary skill in the art. In the disclosed embodiment, the tubing 56 has four off-axis lumens, namely, a first lumen 57 for the cable 46 and the SAS 48, a second lumen 58 for the ring electrode wire pairs 40, 41, a third lumen 59 for irrigation fluid, and a fourth lumen 60 for the support member 50 and the contraction wire 44. Again, position and sizing of the lumens is not critical, except the position of the fourth lumen 60 for the contraction wire 44 is preferably on an inner circumference of the helical form so that proximal movement of the wire can readily contract the helical form. The tubing 56 can be made of any suitable material, and is preferably made of a biocompatible plastic such as polyurethane or PEBAX.

In the depicted embodiment, the pre-formed support or spine member 50 of the distal assembly 17 extends through the fourth lumen 60 of the tubing 56 to define the shape of the helical form 22. The support member 50 is made of a material having shape-memory, i.e., that can be straightened or bent out of its original shape upon exertion of a force and is capable of substantially returning to its original shape upon removal of the force. A particularly preferred material for the support member 50 is a nickel/titanium alloy. Such alloys typically comprise about 55% nickel and 45% titanium, but may comprise from about 54% to about 57% nickel with the balance being titanium. A preferred nickel/titanium alloy is Nitinol, which has excellent shape memory, together with ductility, strength, corrosion resistance, electrical resistivity and temperature stability.

The support member 50 has a cross-section of a predetermined shape that may be generally circular or generally rectangular, including a square shape. It is understood that a generally rectangular cross section can provide greater stiffness compared to a circular cross-section of a comparable size. Moreover, the support member can have a varying thickness along its length, for example, being thinner distally and thicker proximally so that a distal portion can be more readily contracted and a proximal portion can better withstand the load from an axial force that is applied when the distal assembly 17 comes into contact with target tissue.

In one embodiment, the support member 50 has a proximal end just proximal of the junction between the intermediate section 14 and the transitional section 21, for example, about 2-3 mm proximal of the junction in the fifth lumen 37. Alternatively, the support member 50 can extend further proximally into the intermediate section 14 via the fifth lumen or another lumen, the catheter body 12 via the central lumen 18, or further into the control handle 16, as desired or appropriate. In either instance, a nonconductive protective tubing 62 (e.g., a braided polyimide tubing) is provided in surrounding relationship with the support member 50 along its length.

The contraction wire 44 is provided to contract the helical form 22 to reduce its diameter. The contraction wire 44 has a proximal end anchored in the control handle 16, which is used to manipulate the contraction wire. The contraction wire 44 extends through the central lumen 18 of the catheter body 12, through the third lumen 32 of the intermediate section 14, the central lumen of the transitional section 20 and the fourth lumen 60 of the distal assembly 17 to its distal end. In the fourth lumen 60 of the distal assembly 17, the contraction wire 44 extends through the nonconductive protective tubing 62 along with the support member 50. As mentioned, the fourth lumen 60 of the distal assembly 17 is positioned on the side of the helical form 22 closer to its center. With this arrangement, contraction of the helical form 22 is dramatically improved over arrangements where the position of the contraction wire 44 is not so controlled.

In one embodiment, the nonconductive protective tubing 62 comprises three layers, including an inner layer of polyimide over which a braided layer is formed, the braided layer comprising a braided stainless steel mesh or the like, as is generally known in the art. The braided layer enhances the strength of the tubing, reducing the tendency for the contraction wire 44 to straighten the preformed curve of the distal assembly 17. A thin plastic layer of polytetrafluoroethylene is provided over the braided layer to protect the braided layer. The plastic tube 62 has a proximal end anchored to the distal end of the intermediate section 14.

Figure 12:
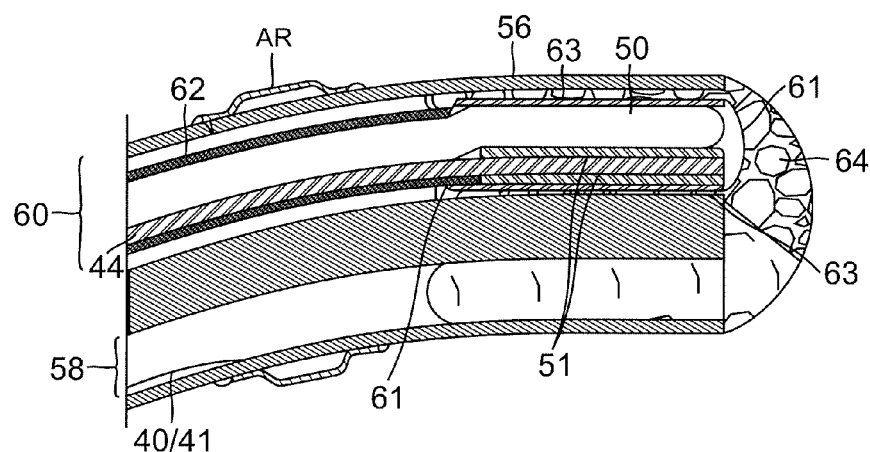
FIG. 12 is a side cross-section view of a distal tip of the distal end portion of FIG. 7, taken along line D-D.

The support member 50 extends through the protective tubing 62 along with the contraction wire 44. In the illustrated embodiment of FIG. 12, the distal ends of the support member 50 and the contraction wire 44 (anchored in a crimped ferrule 51) are soldered at 61 or otherwise attached to a small stainless steel tube 63. With this arrangement, the relative positions of the contraction wire 44 and the support member 50 can be controlled so that the contraction wire 44 can be positioned on the inner side of the helical form 22 closer to the center of the helical form, as described above. The contraction wire 44 on the inside of the curve pulls the support member 50 to the inside of the curve, enhancing contraction of the helical form. Further, when the protective tubing 62 includes a braided layer, it minimizes the risk of the contraction wire 44 tearing through the multi-lumen tubing 56 of the distal assembly 17. In the depicted embodiment, the distal end of the multi-lumen tubing 56 of the distal assembly 17 is sealed closed with a dome 64 of polyurethane glue or the like.

With reference to FIG. 5, the compression coil 45 surrounding the contraction wire 44 extends from the proximal end of the catheter body 12 and through the third lumen 32 of the intermediate section 14. The compression coil has a distal end at or near a mid-location in the transitional section 20. The compression coil 45 is made of any suitable metal, preferably stainless steel, and is tightly wound on itself to provide flexibility, i.e., bending, but to resist compression. The inner diameter of the compression coil is preferably slightly larger than the diameter of the contraction wire 44. The outer surface of the compression coil is covered by a flexible, non-conductive sheath 47, e.g., made of polyimide tubing. The compression coil preferably is formed of a wire having a square or rectangular cross-sectional area, which makes it less compressible than a compression coil formed from a wire having a circular cross-sectional area. As a result, the compression coil 45 keeps the catheter body 12, and particularly the intermediate section 14, from deflecting when the contraction wire 44 is manipulated to contract the distal assembly 17 as it absorbs more of the compression.

Figure 13:
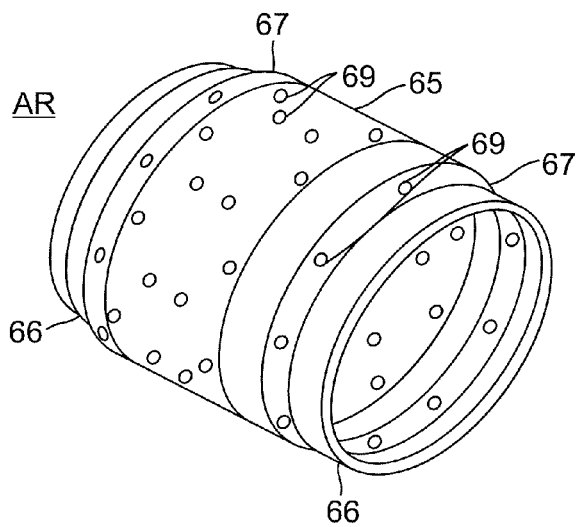
FIG. 13 is a perspective view of an embodiment of an irrigated ablation electrode.
Figure 14:
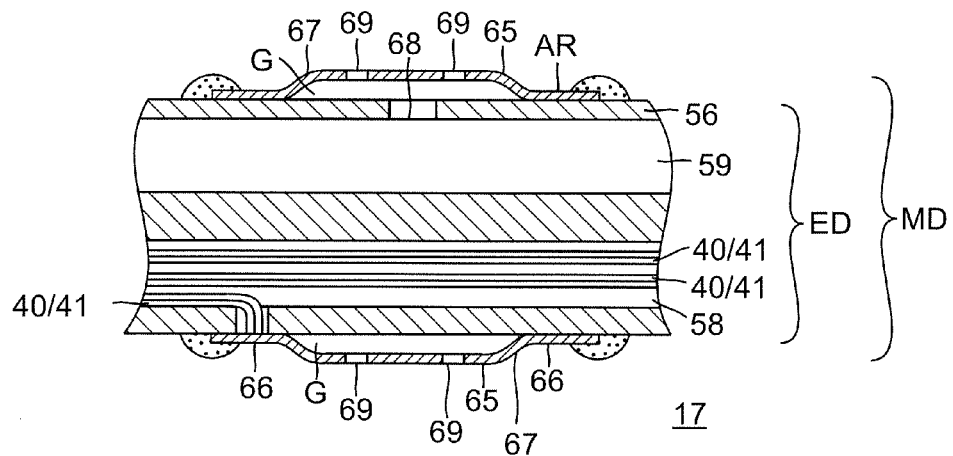
FIG. 14 is a side cross-sectional view of a portion of an embodiment of a distal assembly carrying an irrigated ablation electrode.

A series of ring electrodes 19 are mounted on predetermined locations on the helical form 22, as shown in FIG. 7. The electrodes can be made of any suitable solid conductive material, such as platinum or gold, preferably a combination of platinum and iridium or gold and platinum, and mounted onto the tubing with glue or the like. A suitable embodiment of an electrode adapted for ablation and irrigation is illustrated in FIGS. 13 and 14. The ablation reservoir ("AR") electrode is generally cylindrical with a length greater than its diameter. In one embodiment, the length is about 3.0 mm, the outer diameter is about 2.8 mm, and the inner diameter is about 2.33 mm.

In the illustrated embodiment, the AR electrode has a side cross-section that can resemble a barrel with a side wall 65 (with a width, in one embodiment, of about 2.5 mm) that bulges radially such that a mid portion diameter MD is greater than end diameter ED at opposing end portions 66. Curved transitional regions 67 are provided between the side wall 65 and the end portions 66 to provide an atraumatic profile without corners or sharp edges.

Notably, the mid portion diameter is greater than the outer diameter of the underlying tubing 56 of the distal assembly so that a reservoir or annular gap G exists around the exterior of the tubing 56. The gap G provides improved fluid distribution from the third lumen 59 to the exterior of the AR electrode via an opening 68 provided in the outer wall of the tubing 56 and apertures 69 strategically formed and positioned in the side wall 65 of the AR electrode. The size of the opening 68 in the tubing 56 varies with the position along the length of the helical form 22. For optimum flow, the more distal an opening is along the helical form, the greater the size or cross-section of the opening and/or the plurality of openings for each AR electrode.

The apertures 69 are arranged the side wall 65 of an AR electrode in a predetermined pattern including axially offset rows. These apertures face outwardly promoting flow in a radial direction. Apertures are also provided in or near the curved transitional regions 67 to promote flow in an axial direction. Moreover, these apertures are particularly effective in minimizing charring and coagulation at or near the curved transitional regions which are likely to be "hot spots" resulting from higher current densities due to transitions in the electrode profile. In that regard, the plurality and/or cross-section of the apertures is greater at or near the curved transitional regions than in the side wall of the electrode so as to provide more cooling in the curved transitional regions. As such, the catheter can deliver more irrigation and consequently more cooling without increasing overall flow rate and overall fluid load on the patient.

In one embodiment, there are about 10 apertures on each end portion 66 and about 20 apertures on the side wall 65. The pattern may be adjusted to further improve the flow distribution from each AR electrode. The pattern can be adjusted by adding or removing apertures, modifying the spacing between the apertures, modifying the location of the apertures on the ring electrodes and/or modifying the aperture geometry. Other suitable ring electrodes are described in US Patent Application Publication No. US2010/0168548 A1, the entire content of which is hereby incorporated by reference.

Irrigation fluid is delivered to the distal assembly by the irrigation tubing 43 whose proximal end is attached to a luer hub 100 proximal of the control handle 16 and receives fluid delivered by a pump (not shown). The irrigation tubing extends through the control handle 16, the central lumen 18 of the catheter body 12, the second lumen 34 of the intermediate section 14, the central lumen of the transitional section 20 and a short distance distally into the third lumen 59 of the distal assembly 17, for example, about 5 mm. The fluid enters the third lumen 59 where it exits the lumen via the openings 68 into the reservoir R of the AR electrodes where it exits the reservoir via the apertures 69 to outside of the AR electrodes to minimize charring.

The number of AR electrodes on the distal assembly 17 can vary as desired. Preferably the number of AR electrodes ranges from about six to about twenty, more preferably from about eight to about twelve. In one embodiment, the distal assembly 17 carries ten AR electrodes. The electrodes can be approximately evenly spaced around the helical form 22, as shown in FIG. 7.

The proximal end of each wire 50 is electrically connected to a suitable connector (not shown) distal of the control handle 16 for transmitting and/or receiving electrical signals to accomplish ablation. Each AR electrode is connected to a respective pair of wires 40, 41. In the disclosed embodiment, wire 40 of the wire pair is a copper wire, e.g. a number "40" copper wire. The other wire 41 of the wire pair is a constantan wire. The wires of each pair are electrically isolated from each other except at their distal ends where they are twisted together, fed through a hole formed in the second lumen 58 of the distal assembly 17, and soldered to their respective AR electrode (FIG. 14). The wire pairs for each electrode extend from the control handle 16, through the central lumen 18 of the catheter body 12, the first lumen 33 of the intermediate section 14, the central lumen of the transitional section 20, and the second lumen 58 of the distal assembly 17. Ablation energy, e.g., RF energy, is delivered to the AR electrodes via the wire 40 of the wire pairs. However, the wire pairs inclusive of their respective constantan wire can also function as temperature sensors or thermocouples sensing temperature of each AR electrode.

All of the wire pairs pass through one nonconductive protective sheath 42 (FIG. 6), which can be made of any suitable material, e.g., polyimide, in surrounding relationship therewith. The sheath 42 extends from the control handle 16, the catheter body 12, the intermediate section 14, the transitional section 20 and into the second lumen 58 of the distal assembly 17, terminating just distal of the junction between the transitional section 20 and the distal assembly 17, for example, about 5 mm into the second lumen 58. The distal end is anchored in the second lumen by glue, for example, polyurethane glue or the like.

Figure 15:
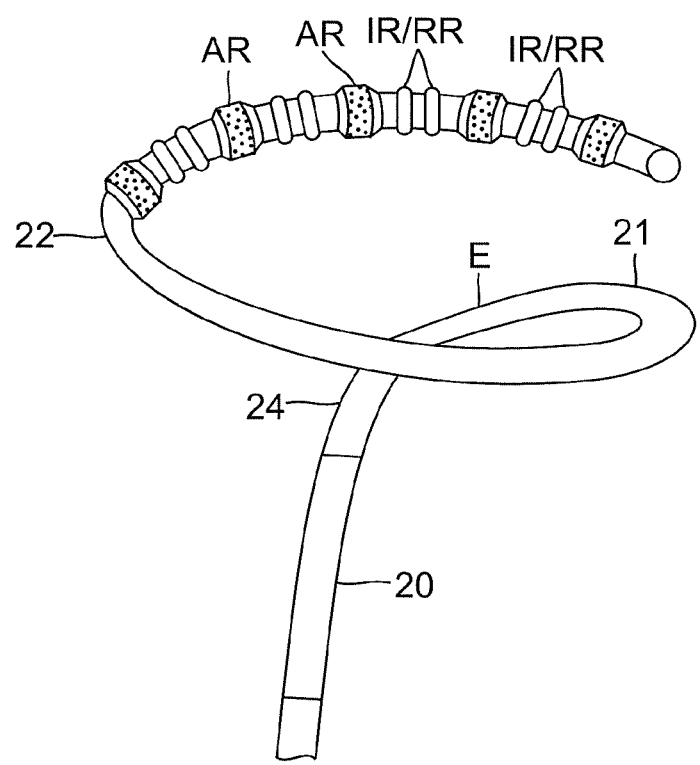
FIG. 15 is a detailed view of another embodiment of a distal assembly carrying electrodes.

An alternate electrode arrangement is depicted in FIG. 15. In this alternate embodiment, the distal assembly 17 has five AR electrodes and includes additional ring electrodes that are narrower than the AR electrodes. Such additional ring electrodes may be impedance recording (IR) electrodes that are electrically isolated from each other and the AR electrodes, and are adapted for recording impedance. In one embodiment of the IR electrodes, the length is about 0.75 mm and the inner diameter is about 2.3 mm. The degree of success of mapping and/or ablation depends on tissue contact. Thus, tissue contact information is particularly useful with multi-electrode ablation catheters. Utilizing at least two independent pairs of IR electrodes (a "pair" hereinafter being any two electrodes, or preferably two most adjacent electrodes) with various size and spacing allows assessment of tissue contact by comparing impedance values and ratio at different frequencies/domains utilizing a single multi-electrode catheter.

The impedance can be further assessed at various frequencies/domains. For example, the ratio of impedance between a pair of IR electrodes and a pair of AR electrodes is used to assess tissue contact in terms of verifying contact and degree or amount of contact. With such isolated bi-polar IR electrodes, the catheter is adapted to perform simultaneous ablation, mapping (electrogram recording) and assessment of tissue contact.

The IR electrodes can be located in between each pair of AR electrodes or selected pairs of AR electrodes depending on the geometry of the distal assembly 17, to provide accurate tissue contact verification via a comparison of the impedance between a pair of isolated (smaller) IR electrodes and the impedance between a pair of (larger) AR electrodes. In the illustrated embodiment of FIG. 15, there are two IR electrodes between each adjacent pair of AR electrodes, for a total of 2(N−1) plurality of IR electrodes for N plurality of AR electrodes.

In another alternate embodiment as also illustrated in FIG. 7, the distal assembly 17 includes electrically isolated bipolar recording ring ("RR") electrodes located in between the AR electrodes to provide improved visualization of pulmonary vein ("PV") potentials. The catheter with such isolated bio-polar RR electrodes permits simultaneous ablation and electrogram recording without the need to reposition the catheter. To minimize far-field effects or any decrease in visualization resolution for more precise electrogram recording of PV potentials, the narrower bi-polar RR electrodes are positioned with a predetermined spacing in between each pair of AR electrodes or in between selected pairs of AR electrodes depending upon the geometry of the distal assembly.

As understood by one of ordinary skill in the art, two closely-spaced RR electrodes allow for more accurate detection of near field PV potential versus far field atrial signals, which is very important when trying to treat atrial fibrillation. Specifically, the near field PV potentials are very small signals whereas the atria, located very close to the pulmonary vein, provides much larger signals. Accordingly, even when the distal assembly 17 is placed in the pulmonary vein, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to better target the locations of myocardial tissue that have PV potentials and therefore allows the clinician to deliver therapy to the specific tissue. Moreover, the closely-spaced electrodes allow the physician to determine the exact anatomical location of the ostium by the electrical signal.

In one embodiment, a pair of AR electrodes are provided between each adjacent pairs of AR electrodes. Thus, for an M plurality of AR electrodes, there are 2(M−1) plurality of RR electrodes. In the illustrated embodiment, the distal assembly 17 carries 10 AR electrodes with a spacing of approximately 4.0 mm between adjacent AR electrodes. Where the distal assembly 17 also carries IR or RR electrodes, they can have a spacing of 1.0 mm between each other. Additionally, the distal most AR electrode can be a different size from the other AR electrodes so as to provide a visually distinguishing signal to the user when the catheter is being viewed under fluoroscopy. Specifically, because the distal assembly 17 is generally circular, it can be difficult for the user to determine the orientation of the helical form 22 and which electrodes are placed at a particular location in the heart. By having one AR electrode, such as the most distal AR electrode, being longer, the user has a reference point when viewing the catheter under fluoroscopy.

For any additional IR or RR electrodes as described above, additional lead wire pairs 40, 41 are provided as appropriate. They extend through the second lumen 58 of the distal assembly 17, the central lumen of the transitional section 20, the first lumen 33 of the intermediate section 14, the central lumen 18 of the catheter body 12 and into the control handle 16.

The deflection puller wire 54 is provided for deflection of the intermediate shaft 14. The deflection wire 54 extends through the central lumen 18 of the catheter body 12 and the sixth lumen 38 of the intermediate section 14. It is anchored at its proximal end in the control handle 16, and at its distal end to a location at or near the distal end of the intermediate section 14 by means of a T-bar 55 (FIGS. 6 and 8) that is affixed to the sidewall of the tubing 15 by suitable material 49 e.g., polyurethane. The distal end is anchored to the sidewall of the tubing 15 of the intermediate section as is generally described in U.S. Pat. No. 6,371,955, the entire disclosure of which is incorporated herein by reference. The puller wire 54 is made of any suitable metal, such as stainless steel or Nitinol, and is preferably coated with Teflon® or the like. The coating imparts lubricity to the puller wire. The puller wire preferably has a diameter ranging from about 0.006 to about 0.010 inch.

A second compression coil 53 is situated within the central lumen 18 of the catheter body 12 in surrounding relation to the puller wire 54 (FIG. 5). The second compression coil 53 extends from the proximal end of the catheter body 12 to at or near the proximal end of the intermediate section 14. The second compression coil 53 is made of any suitable metal, preferably stainless steel, and is tightly wound on itself to provide flexibility, i.e., bending, but to resist compression. The inner diameter of the second compression coil 53 is preferably slightly larger than the diameter of the puller wire 54. The Teflon® coating on the puller wire allows it to slide freely within the second compression coil. Within the catheter body 12, the outer surface of the second compression coil 53 is covered by a flexible, non-conductive sheath 47, e.g., made of polyimide tubing. The second compression coil 53 is anchored at its proximal end to the outer wall 30 of the catheter body 12 by a proximal glue joint and to the intermediate section 14 by a distal glue joint.

Within the sixth lumen 38 of the intermediate section 14, the puller wire 54 extends through a plastic, preferably Teflon®, puller wire sheath, which prevents the puller wire 54 from cutting into the wall of the tubing 15 of the intermediate section 14 when the intermediate section 14 is deflected.

Longitudinal movement of the contraction wire 44 relative to the catheter body 12, which results in contraction of the helical form of the distal assembly 17, is accomplished by suitable manipulation of the control handle 16. Similarly, longitudinal movement of the deflection wire 54 relative to the catheter body 12, which results in deflection of the intermediate section 14, is accomplished by suitable manipulation of the control handle 16. Suitable control handles for manipulating more than one wire are described, for example, in U.S. Pat. Nos. 6,468,260, 6,500,167, and 6,522,933, the disclosures of which are incorporated herein by reference. Suitable control handles for manipulating lasso-type catheters are described in U.S. application Ser. No. 12/550,307, now U.S. Patent Application Publication No. 2011/0054287, filed Aug. 28, 2009, and U.S. application Ser. No. 12/550,204, now U.S. Patent Application Publication No. 2011/0054446, filed Aug. 28, 2009, the entire disclosures of which are incorporated herein by reference.

In one embodiment, the catheter includes a control handle 16 as shown in FIGS. 16 and 17. The control handle 16 includes a deflection control assembly that has a handle body 74 in which a core 76 is fixedly mounted and a piston 78 is slidably mounted over a distal region of the core 76. The piston 78 has a distal portion that extends outside the handle body. A thumb knob 80 is mounted on the distal portion so that the user can more easily move the piston longitudinally relative to the core 76 and handle body 74. The proximal end of the catheter body 12 is fixedly mounted to the distal end of the piston 78. An axial passage 79 is provided at the distal end of the piston, so that various components, including lead wires 40, 41, contraction wire 44, deflection wire 54, sensor cable 46 and irrigation tubing 43 that extend through the catheter body 12 can pass into and if appropriate, through the control handle. For example, the lead wires 40, 41 can extend out the proximal end of the control handle 16 or can be connected to a connector that is incorporated into the control handle, as is generally known in the art.

The proximal end of the deflection wire 54 enters the control handle 16, and is wrapped around a pulley 82 and anchored to the core 76. Longitudinal movement of the thumb knob 80 and piston 78 distally relative to the handle body 74 and core 76 draws the proximal end of the deflection wire 54 distally. As a result, the deflection wire 54 pulls on the side of the intermediate section 14 to which it is anchored, thereby deflecting the intermediate section in that direction. To straighten the intermediate section 14, the thumb knob 80 is moved proximally which results in the piston 78 being moved proximally back to its original position relative to the handle body 74 and core 76.

The control handle 16 is also used for longitudinal movement of the contraction wire 44 by means of a rotational control assembly. In the illustrated embodiment, the rotational control assembly includes a cam handle 71 and a cam receiver 72. By rotating the cam handle in one direction, the cam receiver is drawn proximally to draw on the contraction wire 44. By rotating the cam handle in the other direction, the cam receiver is advanced distally to release the contraction wire. For example, where the helical form 22 has an original outer diameter of about 35 mm, tightening of the helical form by means of the contraction wire can reduce the outer diameter to about 20 mm. The contraction wire 44 extends from the catheter body 12 into the control handle 16, through the axial passage in the piston 78 and through the core 76 to be anchored in an adjuster 75 by which tension on the contraction wire can be adjusted.

In one embodiment, the position sensor 48 includes a plurality of single axis sensors ("SAS") carried on the cable 46 that extends through the first lumen 57 of the distal assembly 17 (FIG. 11), where each SAS occupies a known or predetermined position on the helical form 22. The cable 46 extends proximally from the distal assembly 17 through the central lumen of the transitional section 20, the fourth lumen 36 of the intermediate section 14 (FIG. 6), the central lumen 18 of the catheter body 12, and into the control handle 16. Each SA sensor can be positioned with a known and equal spacing separating adjacent SA sensors. In the disclosed embodiment, the cable carries three SASs that are positioned under the distal-most AR electrode, the proximal-most AR electrode, and a mid AR electrode, for sensing location and/or position of the helical form. Where the distal assembly carries ten AR electrodes, the SASs are under electrodes AR1, AR5 and AR10 (FIG. 7). The SASs enable the helical form to be viewed under mapping systems manufactured and sold by Biosense Webster, Inc., including the CARTO, CARTO XP and NOGA mapping systems. Suitable SASs are described in U.S. application Ser. No. 12/982,765, now U.S. Patent Application Publication No. 2012/0172703, filed Dec. 30, 2010, the entire disclosure of which is incorporated herein by reference.

Figure 18:
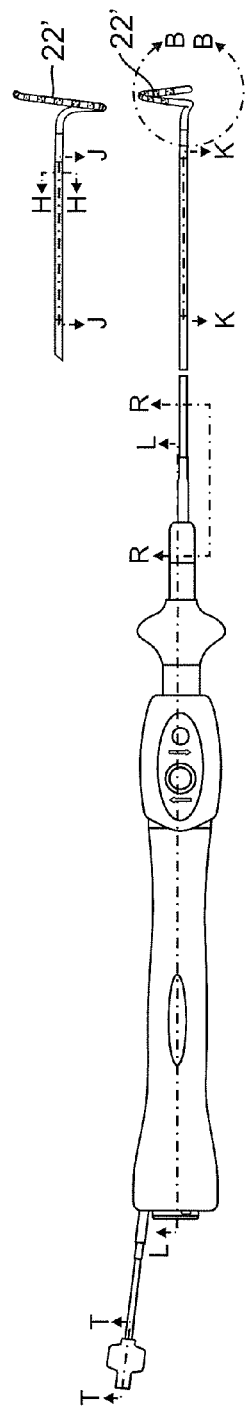
FIG. 18 is a top plan view of an alternate embodiment of a catheter in accordance with the present invention.

In an alternative embodiment of the present invention as illustrated in FIGS. 18 and 19, the distal assembly 17 includes a curved portion that has a semi-circular form or a crescent shape 22'. The semi-circular form 22' has generally the same structure and construction as the helical form 22, except the semi-circular form subtends an angle no greater than about 180 degrees. The circular form is particularly useful where the patient has a larger PV ostium or where two PV are in such close proximity to each other that they share a common ostium. In one embodiment, the outer diameter of the crescent form is about 38.0 to 40.0 mm, which can be reduced to about 20.0 mm when tightened by the contraction wire 44. For example, where the crescent form carries seven AR electrodes, the SASs are located under AR1, AR4 and AR7 (FIG. 19).

Figure 20A:
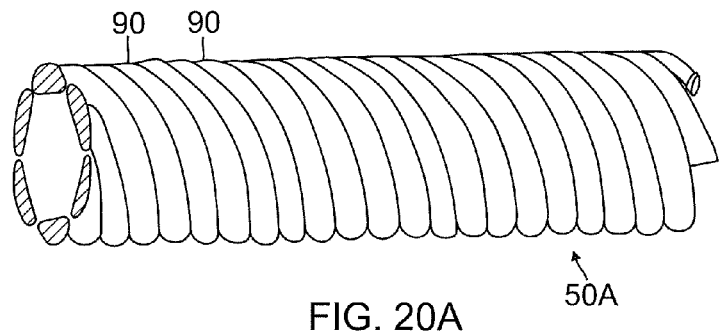
FIG. 20A is a side perspective view of a first embodiment of a hollow shape-memory support member.
Figure 20B:
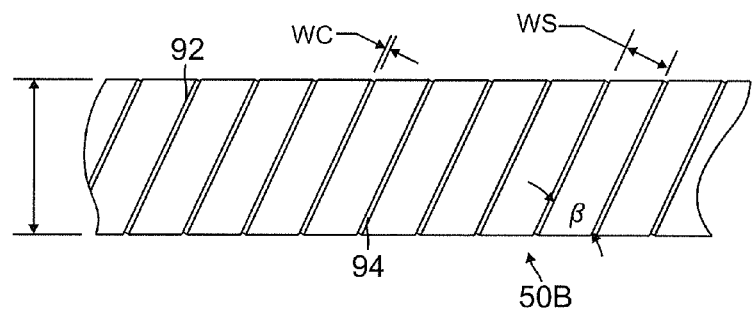
FIG. 20B is a side perspective view of a second embodiment of a hollow shape-memory support member.
Figure 20C:
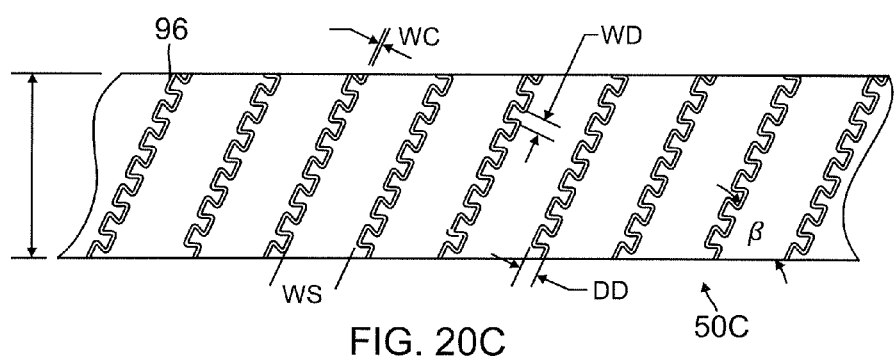
FIG. 20C is a side perspective view of a third embodiment of a hollow shape-memory support member.

In another alternative embodiment of the present invention, as illustrated in FIG. 3, the catheter has a distal assembly 17 whose form 22 (whether it is helical, semi-circular or otherwise) can be varied by means of a stiffener or mandrel 84 that is extended through the shape memory support member 50 of the distal assembly. As illustrated in FIGS. 20A-20C, the shape memory support member 50 is tubular (but not necessarily with a circular cross-section) or otherwise hollow so as to be able to receive the mandrel whose shape and stiffness/flexibility differ from those of the support member 50. In one embodiment as shown in FIG. 20A, the hollow support member 50A includes multiple shape memory wires 90 that are coiled together forming a helical hollow strand tubing. Alternatively, a hollow support member 50B is formed from a tube with a spiral cut 92 (e.g., by laser) along the length of the member to provide greater flexibility. The cut is made at an angle β between about 30-80 degrees, and preferably about 65 degrees, from the axial direction. As shown in FIG. 20B, the spiral cut can be made with a smooth and linear edge 94. In one detailed embodiment, the outer diameter of the member 50B is about 0.25 mm and the inner diameter is about 0.20 mm. The width of a strip WS between adjacent cuts is approx. 0.024 mm and the width of the cut WC is approx. 0.002 mm. Alternatively, as shown in FIG. 20C, the spiral cut can have an interlocking pattern 96, e.g., a dovetail pattern, so that the member can provide greater flexibility without elongation in the axial direction. In one detailed embodiment, the width of a strip WS between adjacent cuts is a bout 0.023 mm. The widest portion of each dovetail WD is about 0.005 mm and the depth of the dovetail DD is about 0.006 mm and the width of the cut WC is about 0.001 mm.

As illustrated in FIG. 3, the generally circular form of the distal assembly (a helical form 22 in this instance) yields to assume the more expanded preformed shape of the mandrel 84 received therein and unwinds to a form with significantly less curvature (shown in solid lines). Upon removal of the mandrel 84 from the distal assembly 17, the helical form 22 reassumes the predetermined shape of the shape memory support member 50 (shown in broken lines).

It is understood that in these embodiments, the hollow support member 50 can extend proximally to at least a proximal portion of the catheter body 12 that remains outside of the patient, if not through control handle 16 so the proximal end is accessible to the operator for inserting the mandrel. The proximal end can exit the catheter body at a location near the control handle or it can extend through the control handle and exit the proximal end of the control handle to be accessed by the operator.

Thus, the operator can expand or even significantly straighten the form of the distal assembly by advancing the mandrel 84 through the hollow support member 50A, 50B, 50C where the mandrel is straighter and stiffer than the hollow shape-memory member. In that regard, it is understood that by providing a mandrel that is stiffer than the shape-memory member of the form of the distal assembly, the form can generally assume the configuration or shape of the mandrel over the configuration of the shape-memory member.

The present catheter 10 is a steerable, multi-electrode, irrigated luminal catheter. The catheter is deployed in a target region of the body, e.g., the atria of the heart, through a guiding sheath. The catheter is designed to facilitate electrophysiological mapping of the target region, e.g., the atria, and to transmit energy, e.g., radiofrequency (RF) current, to the catheter electrodes for ablation purposes. For ablation, the catheter is used in conjunction with a multi-channel RF generator and irrigation pump.

The configuration of the catheter permits the catheter to sit at an opening of a tubular formation, e.g., the PV ostia, with consistent circumferential contact with the tissue. Intracardia signals are recorded by an EP Recording System and the location of the catheter is visualized by fluoroscopy. Once the catheter is in the desired location, energy is delivered (to multiple electrodes simultaneously or selectively) to the veins ostium in unipolar or bipolar mode resulting in PV isolation.

In one embodiment, ablation is delivered at a set wattage on the multi-channel RF generator. During ablation the multi-channel RF generator monitors the temperature of the ring electrode(s) involved and reduces the wattage if the temperature exceeds a value set by the user. The multi-channel RF generator routes the RF current through the selected ring electrodes and catheter temperature information is sent from the thermocouple on the catheter to the generator.

During ablation, an irrigation pump is used to deliver normal heparinized saline to the ring electrodes to cool the ring electrodes to prevent blood from coagulating. The apertures in the ring electrodes facilitate irrigation of the ablation areas of the catheter. Where deeper lesions are desired, the greater flow distribution (without greater flow rate) of each ring electrode via the apertures reduces the increased risk of charring and coagulum on the ablation surfaces that would normally be encountered when the amount of power delivered to the electrode/tissue interface is increased. A greater flow distribution from each ring electrode which leads to improved irrigation efficiency offers advantages, including (1) higher power delivery without increasing fluid pump flow rate, (2) ability to use currently available, flow rate-limited pumps, (3) eliminate need to use multiple pumps, and/or (4) reduction in fluid load on patient during ablation procedure.

Figure 21:
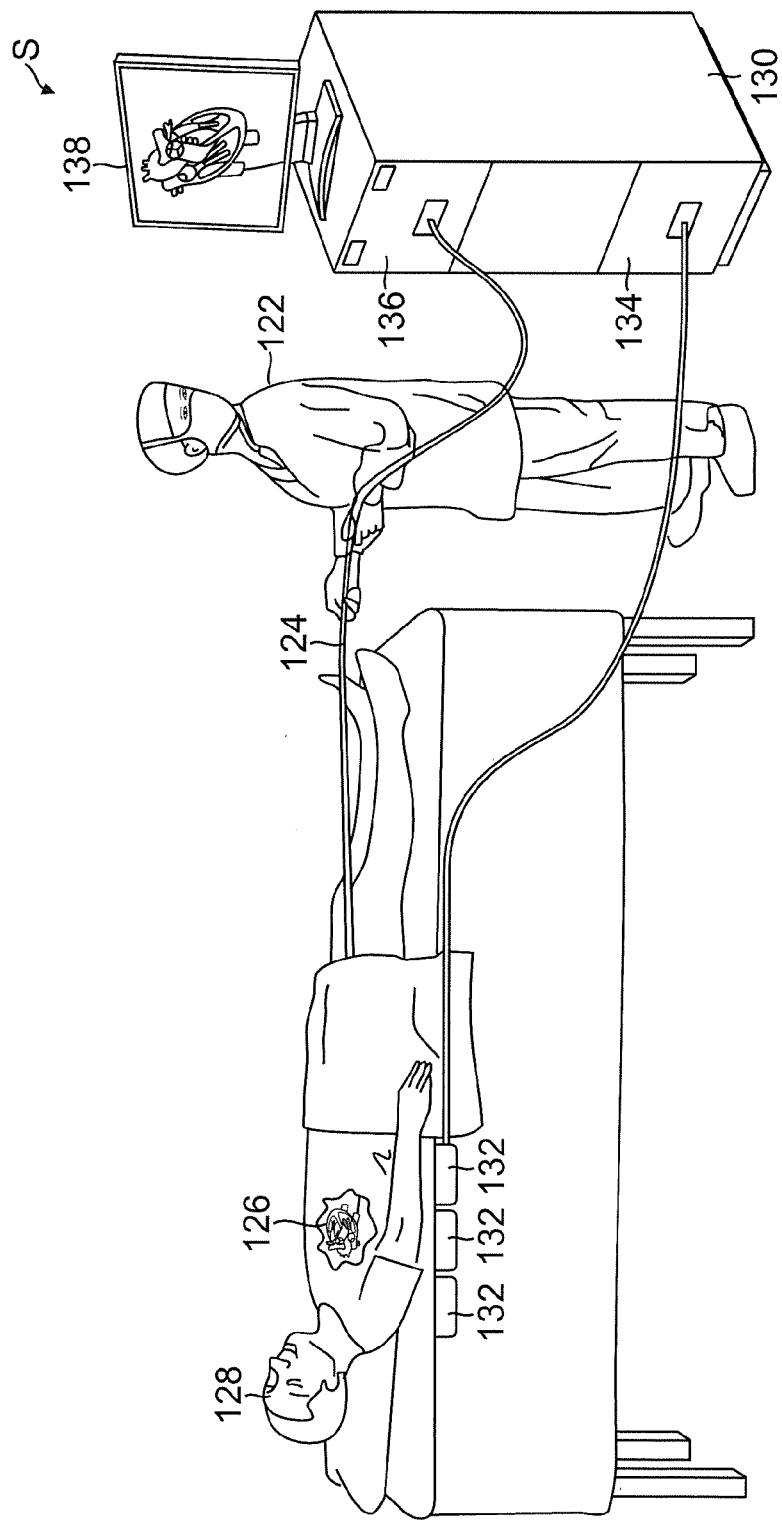
FIG. 21 is a schematic pictorial illustration of a system for ablation of tissue in the heart, in accordance with an embodiment of the present invention.

FIG. 21 is a schematic pictorial illustration of a system S for ablation of tissue in a heart 126 of a patient 128, in accordance with an embodiment of the present invention. An operator 122, such as a cardiologist, inserts a catheter 124 through the vascular system of the patient so that the distal end of the catheter enters a chamber of the patient's heart. Operator advances the catheter so that the end section 222 of the catheter engages endocardial tissue at a desired location or locations, as shown in FIG. 21. Catheter 124 is connected by a suitable connector at its proximal end to a console 130. The console comprises an RF generator for applying RF energy through electrodes on the end section of the catheter in order to ablate the tissue contacted by the distal section. Alternatively or additionally, catheter may be used for other diagnostic and/or therapeutic functions, such as intracardiac electrical mapping or other types of ablation therapy.

In the pictured embodiment, system S uses magnetic positioning sensing to determine position coordinates of the distal assembly of the catheter inside heart. To determine the position coordinates, a driver circuit 134 in console 130 drives field generators 132 to generate magnetic fields within the body of patient. Typically, field generators comprise coils, which are placed below the patient's torso at known positions external to the body. These coils generate magnetic fields in a predetermined working volume that contains heart. One or more magnetic field sensors within the end section of catheter generate electrical signals in response to these magnetic fields. The console 130 processes these signals in order to determine the position (location and/or orientation) coordinates of the distal assembly 222 of the catheter, and possibly also the deformation of the distal assembly, as explained below. Console may use the coordinates in driving a display 138 to show the location and status of the catheter. This method of position sensing and processing is described in detail, for example, in PCT International Publication WO 96/05768, whose entire disclosure is incorporated herein by reference, and is implemented in the CARTO system produced by Biosense Webster Inc. (Diamond Bar, Calif.).

Alternatively or additionally, system may comprise an automated mechanism (not shown) for maneuvering and operating catheter within the body of patient. Such mechanisms are typically capable of controlling both the longitudinal motion (advance/retract) and the rotation of catheter. In such embodiments, console generates a control input for controlling the motion of the catheter based on the signals provided by the position sensing system.

Although FIG. 21 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter that causes console to receive signals indicative of the coordinates of the element. The position transducer may thus comprise a receiver in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

Figure 22:
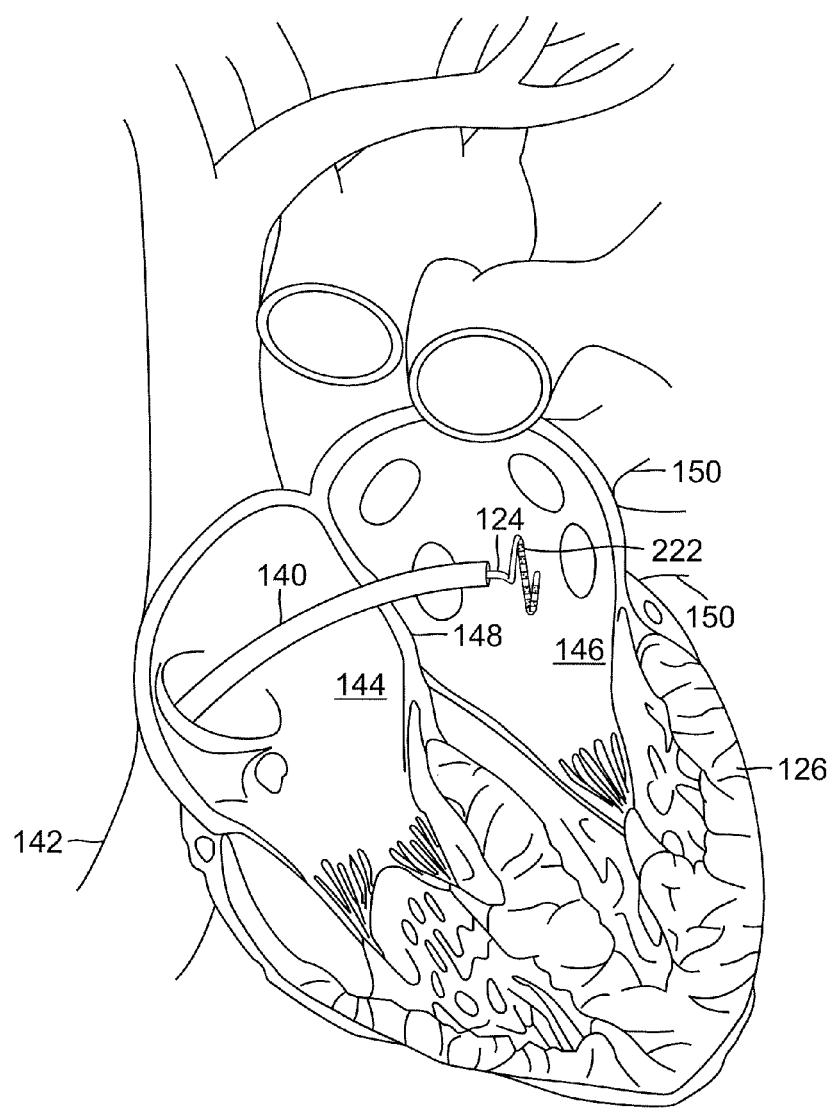
FIG. 22 is a schematic sectional view of a heart showing insertion of a catheter into the left atrium, in accordance with an embodiment of the present invention.

FIG. 22 is a schematic sectional view of heart 126, showing insertion of catheter 124 into the heart, in accordance with an embodiment of the present invention. To insert the catheter in the pictured embodiment, the operator first passes a sheath 140 percutaneously through the vascular system and into right atrium 144 of the heart through ascending vena cava 142. The sheath penetrates through interatrial septum 148, typically via the fossa ovalis, into left atrium 146. Alternatively, other approach paths may be used. Catheter is then inserted through the sheath until an end section 222 of the catheter passes out of the distal opening of the end of the sheath 140 into the left atrium 146.

Operator aligns the longitudinal axis of sheath 140 (and of catheter) inside left atrium 146 with the axis of one of pulmonary veins. He may use the thumb knob 80 of the control handle 16 to deflect the intermediate section 14 in directing the distal assembly 222 toward the target ostium. The operator may carry out this alignment using the position sensing methods described above, along with a pre-acquired map or image of heart. Alternatively or additionally, the alignment may be performed under fluoroscopic or other means of visualization. The operator advances the catheter toward the target pulmonary vein so that the distal assembly 222 contacts the ostium and either partly or fully surrounds the vein. By manipulating the cam handle 71, the helical form of the distal assembly 222 is contracted to fit the PV ostium. In the disclosed embodiment, the contraction wire 44 is drawn proximally by the cam receiver 72 to tighten and decrease the diameter of the helical form when the cam handle is turned in one direction. By turning the cam handle in the opposition direction, the cam receiver releases the contraction wire to allow the helical form to expand and return to its original diameter.

The operator can then rotate the catheter about its axis within the sheath so that the distal assembly traces an annular path around the inner circumference of the vein. Meanwhile, the operator actuates RF generator to ablate the tissue in contact with the AR electrodes along the path. Simultaneously, impedance and/or PV potential recordings can be made with the IR and/or RR electrodes. After completing this procedure around one pulmonary vein, the operator may shift the sheath and catheter and repeat the procedure around one or more of the other pulmonary veins.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated body having a longitudinal axis;
   a distal assembly distal the elongated body, the distal assembly having a shape-memory support member, a helical form and a transverse section, the transverse section connecting the helical form to the elongated body and being generally transverse to the longitudinal axis of the elongated body;
   at least one irrigated ablation ring electrode mounted on the helical form;
   a control handle proximal the elongated body;
   wherein the helical form has an off-edge configuration such that the longitudinal axis of the elongated body does not intersect a circumference of the helical form, and an off-axis configuration such that a longitudinal axis of the helical form is axially offset from the longitudinal axis of the elongated body, and wherein the generally transverse section of the distal assembly lies on a nondiametrical chord of the helical form.

2. A catheter of claim 1, further comprising a contraction wire extending through the elongated body and the distal assembly, wherein the control handle includes a first control member configured to actuate the contraction wire to contract the helical form.

3. A catheter of claim 1, further comprising a deflection wire extending through the elongated body, wherein the control handle includes a second control member configured to actuate the deflection wire to deflect a portion of the elongated body.

4. A catheter of claim 1, wherein the shape-memory support member is hollow.

5. A catheter of claim 4, further comprising a mandrel adapted for insertion through the shape-memory support member, wherein the mandrel has a different form from the helical form.

6. A catheter of claim 1, wherein the irrigated ablation ring electrode has at least one aperture configured to pass fluid from inside the ring electrode to outside the ring electrode in a radial direction.

7. A catheter of claim 1, wherein the irrigated ablation ring electrode has at least one aperture configured to pass fluid from inside the ring electrode to outside the ring electrode in an axial direction.

8. A catheter of claim 1, further comprising at least one ring electrode adapted to measure impedance.

9. A catheter of claim 1, further comprising at least one ring electrode adapted to measure PV potentials.

10. A catheter comprising:
    an elongated body having a longitudinal axis;
    a distal assembly distal the elongated body, the distal assembly having a hollow support member, a first predetermined form comprising a helical form, and a transverse section, the transverse section connecting the helical form to the elongated body and being generally transverse to the longitudinal axis of the elongated body, wherein the helical form has an off-edge configuration such that the longitudinal axis of the elongated body does not intersect a circumference of the helical form, and an off-set configuration such that a longitudinal axis of the helical form is axially offset from the longitudinal axis of the elongated body, and wherein the generally transverse section of the distal assembly lies on a non-diametrical chord of the helical form;
    at least one electrode mounted on the distal assembly;
    a control handle proximal the elongated body; and
    a mandrel defining a second predetermined form, the mandrel being adapted for insertion into the hollow support member.

11. A catheter of claim 10, wherein the first predetermined form of the distal assembly has a curvature and the second predetermined form of the mandrel has a curvature, and wherein the curvature of the distal assembly is greater than the curvature of the mandrel.

12. A catheter of claim 10, wherein the support member comprises a hollow support member that includes a hollow strand tubing.

13. A catheter of claim 10, wherein the support member comprises a hollow support member that includes a tubular member with a spiral cut along its length.

14. A catheter of claim 13, wherein the spiral cut includes an interlocking pattern.

* * * * *